(12) United States Patent
Gerber

(10) Patent No.: US 9,061,146 B2
(45) Date of Patent: Jun. 23, 2015

(54) IMPEDANCE-BASED BLADDER SENSING

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1826 days.

(21) Appl. No.: 11/261,443

(22) Filed: Oct. 28, 2005

(65) Prior Publication Data

US 2007/0100387 A1 May 3, 2007

(51) Int. Cl.
| | | |
|---|---|---|
| *A61N 1/32* | (2006.01) | |
| *A61N 1/36* | (2006.01) | |
| *A61B 5/053* | (2006.01) | |
| *A61B 5/00* | (2006.01) | |
| *A61N 1/372* | (2006.01) | |
| *A61B 5/20* | (2006.01) | |

(52) U.S. Cl.
CPC ............ *A61N 1/36007* (2013.01); *A61B 5/053* (2013.01); *A61B 5/0538* (2013.01); *A61B 5/20* (2013.01); *A61B 5/204* (2013.01); *A61B 5/6874* (2013.01); *A61N 1/37252* (2013.01)

(58) Field of Classification Search
USPC ....................................... 607/40, 41; 600/547
See application file for complete search history.

(56) References Cited

U.S. PATENT DOCUMENTS

| | | | |
|---|---|---|---|
| 3,662,758 A | | 5/1972 | Glover |
| 5,103,835 A | * | 4/1992 | Yamada et al. ............... 600/547 |
| 6,354,991 B1 | | 3/2002 | Gross et al. |
| 6,360,123 B1 | | 3/2002 | Kimchi et al. |
| 6,393,323 B1 | | 5/2002 | Sawan et al. |
| 6,652,449 B1 | | 11/2003 | Gross et al. |
| 6,689,056 B1 | * | 2/2004 | Kilcoyne et al. ............... 600/300 |
| 6,735,474 B1 | | 5/2004 | Loeb et al. |
| 6,911,912 B2 | | 6/2005 | Roe |
| 6,941,171 B2 | | 9/2005 | Mann et al. |
| 2002/0055761 A1 | * | 5/2002 | Mann et al. ..................... 607/41 |

(Continued)

FOREIGN PATENT DOCUMENTS

| | | |
|---|---|---|
| JP | 05-038346 | 2/1993 |
| WO | WO 03/099118 A1 | 12/2003 |
| WO | WO 2005/077276 | 8/2005 |

OTHER PUBLICATIONS

Coosemans, J., Puers, R., "Datalogger for Bladder Pressure Monitoring with Wireless Power and Data Transmission," Belgian Day on Biomedical Engineering, (1 page), Oct. 17, 2003.

(Continued)

*Primary Examiner* — Carl H Layno
*Assistant Examiner* — Jennifer Ghand
(74) *Attorney, Agent, or Firm* — Shumaker & Sieffert, P.A.

(57) ABSTRACT

Systems that sense the volume, activity or other parameters of the urinary bladder are described. The systems include at least two electrodes that are implanted at respective locations proximate the wall of the bladder, and may be located substantially opposite each other with respect to a center of the bladder. At least one of the electrodes receives an electrical signal emitted by another of the electrodes. Systems according to the invention detect an impedance through the bladder based on the signal, e.g., based on one or both of the current or voltage of the signal. Based on the detected impedance, the systems sense one or more parameters of the bladder, such as volume, activity, or the like, which influence the impedance. The detected impedance, or bladder parameter information derived from the impedance, may be stored for short- or long-term monitoring, or used to control delivery of a therapy to a patient.

42 Claims, 10 Drawing Sheets

(56) References Cited

U.S. PATENT DOCUMENTS

| | | | |
|---|---|---|---|
| 2002/0062060 | A1 | 5/2002 | Gross et al. |
| 2002/0103424 | A1 | 8/2002 | Swoyer et al. |
| 2003/0100930 | A1 | 5/2003 | Cohen et al. |
| 2005/0113877 | A1 | 5/2005 | Spinelli et al. |
| 2005/0113878 | A1 | 5/2005 | Gerber |
| 2005/0146436 | A1 | 7/2005 | Roe |
| 2005/0177067 | A1 | 8/2005 | Tracey et al. |
| 2005/0192635 | A1 | 9/2005 | Creasey et al. |
| 2005/0245840 | A1 | 11/2005 | Christopherson et al. |
| 2005/0245971 | A1* | 11/2005 | Brockway et al. ............ 607/2 |
| 2006/0122659 | A9 | 6/2006 | Gerber |
| 2006/0190046 | A9 | 8/2006 | Gerber |
| 2006/0211951 | A1 | 9/2006 | Milijasevic et al. |
| 2007/0010761 | A1* | 1/2007 | Mo .......................... 600/581 |

OTHER PUBLICATIONS

Siwapornsathain, E., Lal, A., Binard, J., "A Telemetry and Sensor Platform for Ambulatory Urodynamics," Department of Electrical and Computer Engineering, University of Wisconsin, Madison, (5 pages), 2002.

MEMSCAP, "Wireless Physiological Pressure Transducer," (2 pages), May 2003; www.memscap.com.

Van Waalwijk van Doorn, E., Anders, K. Khullar V., Kulseng Hanssen, S., Pesce, F., Robertson, A., Rosario, D., Schafer, W., "Standardisation of Ambulatory Urodynamic Monitoring," Report of the Standardisation Sub-committee of the ICS for ambulatory urodynamic studies, (21 pages), published in Neurol. Urodyn. 19(2), pp. 113-125, 2000.

Provost et al. "Proposed new bladder volume monitoring device based on impedance measurement" Medical and Biological Engineering and Computing, Springer, Heildelberg, DE, vol. 35, No. 6, pp. 691-694, Nov. 1997.

European Office Action dated May 13, 2009 for corresponding European Patent Application No. 06839605.0 (4 pgs.).

International Search Report from International Application No. PCT/US2006/060344, mailed Jul. 19, 2007, 5 pp.

Written Opinion International Application No. PCT/US2006/060344, mailed Jul. 19, 2007, 9 pp.

International Preliminary Report on Patentability from International Application No. PCT/US2006/060344, dated Apr. 29, 2008, 10 pp.

Communication pursuant to Rules 161 and 162 EPC from counterpart European Application No. 06839605.0-2305, dated Jun. 9, 2008, 2 pp.

Response to European Office Action dated May 13, 2009, from counterpart European Application No. 06839605.0-2305, filed on Nov. 19, 2009, 3 pp.

* cited by examiner

IMPEDANCE-BASED BLADDER SENSING

TECHNICAL FIELD

The invention relates to implantable medical devices and, more particularly, implantable sensors.

BACKGROUND

Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance, and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients may also suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence. As used herein, the term "urinary incontinence" include disorders in which urination occurs when not desired, such as stress or urge incontinence, and disorders in which urination does not occur as desired, such as urinary retention disorder.

Therapies for treating urinary incontinence include delivery of electrical stimulation and delivery of therapeutic substances. For example, delivery of electrical stimulation from an implantable medical device to nerves in the pelvic floor, such as the sacral and pudendal nerves, may provide an effective therapy for urinary incontinence. Electrical stimulation of the sacral nerve may induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

SUMMARY

In general, the invention is directed to systems and associated methods for sensing the volume, activity, or other parameters of the urinary bladder based on an impedance through the bladder. Systems according to the invention emit and receive an electrical signal through the bladder, and determine the impedance through the bladder based on the signal. The electrical signal varies as a function of the impedance through the bladder, which may in turn vary as a function of volume, activity, or other parameters of the bladder.

Systems according to the invention include at least two electrodes that respectively emit and receive the electrical signal. The electrodes are implanted proximate to the wall of the bladder at respective locations, and may be located substantially opposite each other relative to a center of the bladder. As examples, the electrodes may be coupled to an implantable medical device (IMD) that is implanted outside of the bladder by respective leads, or may be coupled to an implantable module that is attached to the bladder wall. Electrodes coupled to such an implantable module may be formed on or within a housing of the module, or coupled to the module by leads. In embodiments that include an implantable module, the module may wirelessly transmit information based on the detected impedance, e.g., information related to the filling or emptying of the bladder, to one or more of an implantable medical device or external device, such as an external programmer.

Some embodiments of the invention include delivering a therapy to alleviate urinary incontinence, such electrical stimulation or a therapeutic substance, based on detected impedance. For example, some embodiments may include an implantable medical device that delivers a therapy based on the detected impedance. In some embodiments, an implantable module wirelessly transmits information relating to the detected impedance to an implantable medical device that delivers the therapy, and the implantable medical device delivers therapy based on the transmitted information. In other embodiments, the implantable module transmits the information to an external programmer, which controls delivery of therapy by an implantable medical device based on the information received from the implantable module. In various embodiments, the systems may provide closed-loop feedback control of the therapy based on the detected impedance, trigger or terminate the therapy based on the impedance, or both.

Some embodiments may present information relating to filling, emptying, volume, activity, or other parameters of the bladder to a user based on the detected impedance. Systems according to the invention may include an external programmer or other external device with a user interface for presenting such information to the user. The external device may receive information related to the detected impedance from an implantable medical device or implantable module, and present information relating to filling, emptying, volume, activity, or other parameters of the bladder to a user based on the received information. The implantable medical device or module may include a memory to store information relating to the bladder impedance over time, for later retrieval by an external device. In this manner, systems according to the invention may provide short- or long-term monitoring of bladder functioning, e.g., for diagnosis or monitoring of urinary incontinence. Further, systems according to the invention may provide alerts to the patient relating to the volume of fullness of the bladder, or incontinence events.

In one embodiment, the invention is directed to a method comprising emitting an electrical signal from a first electrode implanted proximate to a wall of a bladder of a patient at a first location, receiving the electrical signal via a second electrode implanted proximate to the wall of the bladder at a second location, and detecting an impedance through the bladder based on the signal.

In another embodiment, the invention is directed to a system comprising a first electrode implanted proximate to a wall of a bladder of a patient at a first location that emits an electrical signal, a second electrode implanted proximate to the wall of the bladder at a second location that receives the electrical signal, and impedance measurement circuitry that emits an electrical signal via the first electrode, receives the electrical signal via the second electrode, and detects an impedance through the bladder based on the signal.

In another embodiment, the invention is directed to a system comprising an implantable module implanted on or within a wall of a bladder of a patient, a first electrode electrically coupled to the implantable module and located proximate to a wall of the bladder at a first location, and a second electrode electrically coupled to the implantable module and located proximate to the wall of the bladder at a second location. The implantable module emits an electrical signal via the first electrode, receives the electrical signal via the second electrode, and detects an impedance through the bladder based on the signal.

In various embodiments, the invention may provide one or more advantages. For example, while placing electrodes on or within the bladder may be more invasive than other sensors, and particularly, external sensors, it may allow systems according to the invention to provide more accurate information regarding bladder volume, activity, and the like. Placing electrodes on or within the bladder may also facilitate pH monitoring in addition to bladder volume and activity monitoring, in some embodiments. According to some embodiments, electrodes may be placed in the bladder without surgery, e.g., endoscopically via the urethra as part of an implantable module.

In some embodiments, therapy delivery may be responsive to detected bladder fullness levels and/or urinary incontinence events. In addition, in some embodiments, the system may notify the patient of a filled bladder and urge the patient to urinate before causing an unintentional voiding event, or before the fullness of bladder results in pelvic pain, e.g., due interstitial cystitis. Also, with closed-loop therapy, the system may generate stimulation parameter adjustments, based on sensed bladder conditions, to more effectively target the function of the urinary sphincter muscle or pelvic floor muscle tone, thereby enhancing therapy efficacy. In some patients, more effective stimulation via the sacral or pudendal nerves may actually serve to strengthen the sphincter muscle or enhance pelvic floor tone, restoring proper operation.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
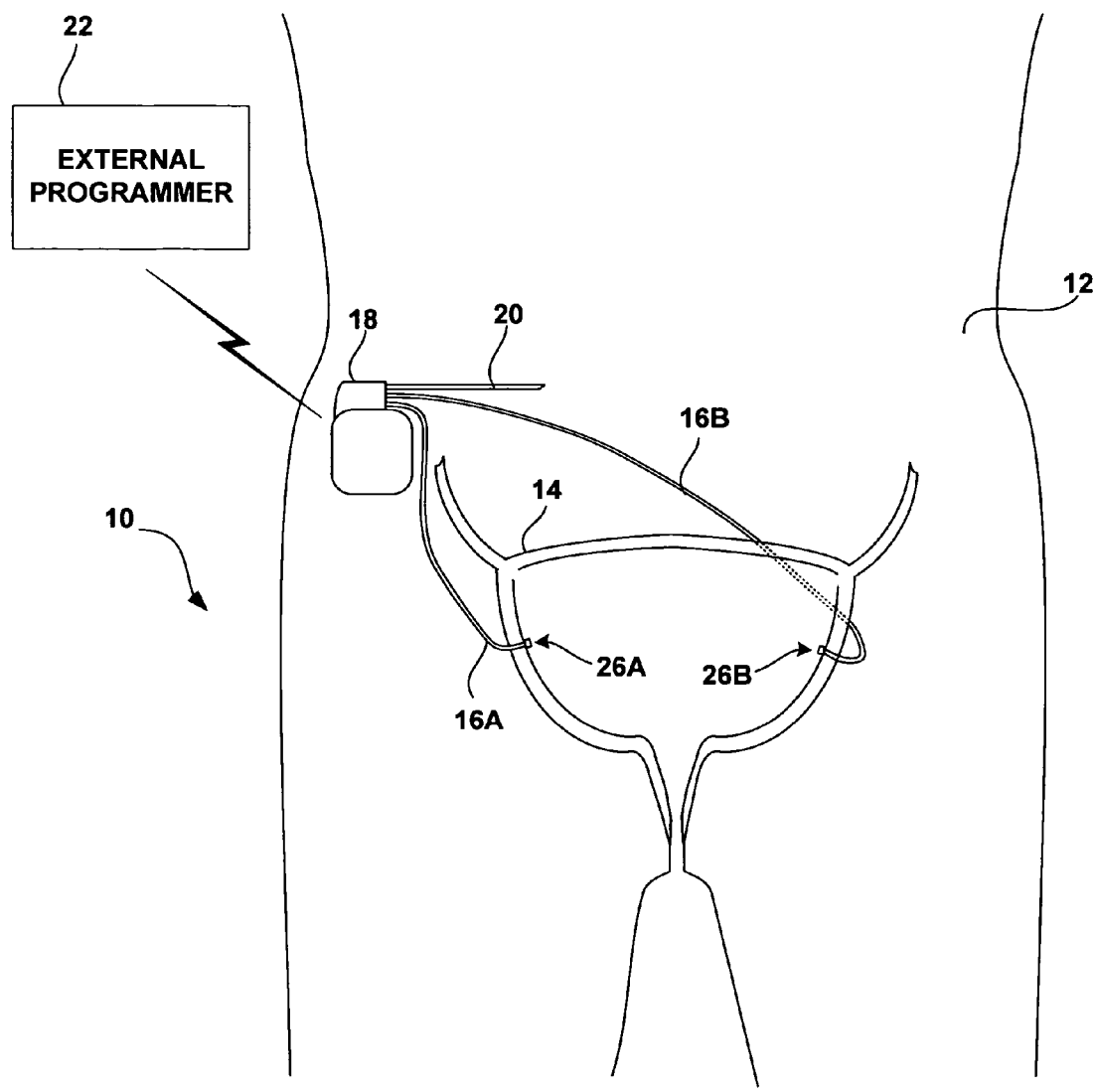
FIG. 1 is a schematic diagram illustrating an example system that senses parameters of the bladder based on an impedance through the bladder.

FIG. 1 is a schematic diagram illustrating an example system 10 that senses parameters of a bladder 14 of a patient 12 based on a detected impedance through the bladder. As shown in FIG. 1, system 10 may include an implantable medical device (IMD) 18 and external programmer 22. System 10 may provide short- or long-term monitoring of bladder functioning or urinary incontinence based on the detected impedance, or use the detected signal as feedback to control delivery of a therapy for alleviating urinary incontinence.

In the illustrated embodiment, IMD 18 is coupled to first and second electrodes 26A and 26B (collectively "electrodes 26") via a first and second leads 16A and 16B (collectively "leads 16"). Leads 16 penetrate the wall of bladder 14, and locate the electrode proximate to an interior surface of the wall of the bladder at first and second locations, respectively. Electrodes 26 are located at respective locations, and may be located substantially opposite each other relative to the center of bladder 14. In some embodiments, one or both of leads 16 need not penetrate the wall of bladder 16, and one or both of electrodes 26 may be located proximate to the exterior surface of the bladder wall. Further, in some embodiments, a common lead 16 may carry both electrodes 26 to respective locations proximate to the bladder wall.

IMD 18 may transmit an electrical signal through bladder 14 via leads 16 and electrodes 26. The detected signal varies as a function of an impedance through bladder 14, which in turn may vary based on a variety of parameters of the bladder, including volume, activity, and pH. Accordingly, IMD 18 detects an impedance through bladder 14 based on the signal. In some embodiments, IMD 18 may transmit information related to the detected impedance, such as measured samples or bladder parameter information determined based on the samples, to external programmer 22.

System 10, e.g., IMD 18 or external programmer 22 may monitor bladder volume, filing, fill level, emptying, contractions, and the like based on the detected impedance. A fill level or rate of volume change may be considered bladder activity or bladder condition information, as described herein. Based on the detected impedance, IMD 18 or external programmer 22 may initiate, terminate or adjust a therapy delivered by IMD 18. Further, external programmer 22 or another computing device with a user interface may present bladder volume, activity or function information to a user, such as a physician, based on the detected impedance. In some embodiments, IMD 18 or external programmer 22 may store information related to the detected impedance or bladder parameters derived from the detected impedance for long- or short-term monitoring of bladder volume, activity or function, e.g., for evaluation of urinary incontinence or monitoring the efficacy a treatment for urinary incontinence. In some embodiments, IMD 18 or programmer 22 may provide closed loop feedback control of delivery of therapy by IMD 18 to patient 12 based on the detected impedance.

In the illustrated example, IMD 18 is coupled to a stimulation lead 20, which may include one or more electrodes as is known in the art for delivering electrical stimulation to patient 12. Lead 20 may be tunneled from IMD 18 to one or more pelvic floor nerve or muscle sites associated with the urinary system. For example, stimulation lead 20 may terminate adjacent nerves in the pelvic floor, such as the sacral or pudendal nerves which innervates the pelvic floor muscles including the urinary sphincter. For example, sacral or pudendal nerve stimulation may result in an increase in pelvic floor muscle tone or the contraction of the urinary sphincter, which keeps urine inside bladder 14. Appropriate nerve stimulation may assist patient 12 in avoiding urinary incontinence, or promoting the elimination of urine from bladder 14 when urination is desired.

In other embodiments, IMD 16 additionally or alternatively delivers one or more therapeutic substances to patient 12 via one or more catheters. Therapeutic substances may include pharmaceutical, chemical or genetic substances. Such substances may be delivered to pelvis floor nerves or muscles associated with urination.

In either case, patient 12 may control the therapy delivered by IMD 18 via programmer 22. For example, patient 12 may initiate or terminate delivery of therapy by IMD 18 via programmer 22. Further, IMD 18 or external programmer 22 may control delivery of therapy based on the bladder parameters that affect the impedance through the bladder by initiating, adjusting, or terminating the therapy based on the impedance detected by IMD 18. For example, IMD 18 or external programmer 22 may adjust electrical stimulation parameters such as pulse amplitude, rate and width, and electrode polarity or configuration, based on the detected impedance. As another example, IMD 18 or external programmer 22 may similarly adjust the infusion rate, concentration or number of substances delivered to patient 12 based on the detected impedance.

If the detected impedance indicates increased bladder volume, which may result in increased pressure on the pelvic floor muscles and urinary sphincter muscle, the IMD or programmer may increases the intensity of therapy intended to promote urinary retention. After a voiding event, the IMD or programmer may terminate or reduce the intensity of the therapy to conserve power or other resources. In some embodiments, external programmer 22 may alert patient 12 if bladder volume reaches a threshold based on the detected impedance. In response, patient 12 may use programmer to terminate a therapy intended to promote urinary retention and/or initiate a therapy intended to promote urination. Alerting the patient when the bladder volume reaches a threshold may advantageously allow a patient to avoid an incontinence event, or pelvic pain in cases where the patient has a condition such that a relatively full bladder causes pelvic pain, such as interstitial cystitis. In some embodiments, therapy may be delivered substantially continuously, but at different intensities based on the detected impedance.

External programmer 22 may be a small, battery-powered, portable device that accompanies patient 12 throughout a daily routine. Programmer 22 may have a simple user interface, such as a button or keypad, and a display or lights. Patient 12 may voluntarily initiate a voiding event, i.e., a voluntary voiding of bladder 14, via the user interface. In this case, programmer 22 may transmit a command signal to IMD 18 to temporarily suspend stimulation, and thereby permit voluntary voiding. In some embodiments, the length of time for a voiding event may be determined by pressing and holding down a button for the duration of a voiding event, pressing a button a first time to initiate voiding and a second time when voiding is complete, or by a predetermined length of time permitted by programmer 22 or IMD 18. In each case, programmer 22 causes implantable IMD 18 to temporarily suspend stimulation so that voluntary voiding is possible. However, in other embodiments, suspension of stimulation is not necessary to facilitate voiding, and stimulation may occur substantially continuously, with modifications based on the detected impedance.

IMD 18 may be surgically implanted at a site in patient 12 near the pelvis. The implantation site may be a subcutaneous location in the side of the lower abdomen or the side of the lower back or upper buttocks. One or more electrical stimulation leads 20 may be connected to IMD 18 and surgically or percutaneously tunneled to place one or more electrodes carried by a distal end of the lead at a desired pelvic nerve or muscle site, such as a sacral or pudendal nerve site. IMD 18 has a biocompatible housing, which may be formed from titanium, stainless steel or the like. IMD 18 may be configured to deliver electrical stimulation pulses with a range of electrical parameter values, such as amplitude, pulse width and pulse rate, selected to prevent involuntary leakage of urine from bladder 14.

The invention is not limited to embodiments that include a therapy-delivering IMD. In some embodiments, as will be discussed in greater detail below, an implantable sensor module may detect impedance and store information relating to the detected impedance without delivery of therapy, for short or long-term monitoring of bladder function, e.g., for a urinary incontinence study.

Figure 2:
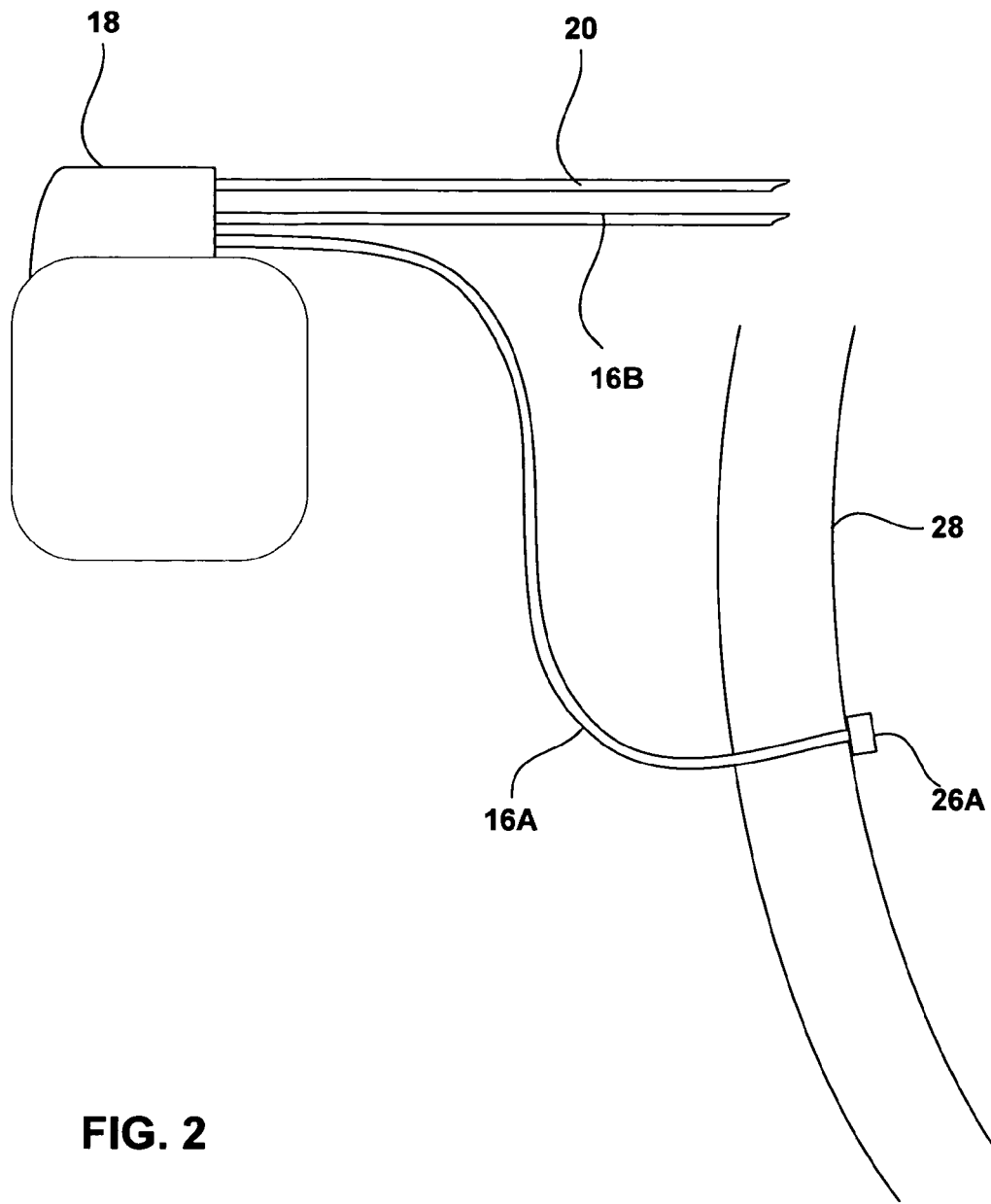
FIG. 2 is an enlarged view of an implantable stimulator with a lead penetrating a bladder wall to dispose an electrode within the bladder.

FIG. 2 is an enlarged view of IMD 18 and lead 16A penetrating a bladder wall to dispose electrode 26A within bladder 14 proximate to the interior surface of the bladder wall at a first location. Although not illustrated in FIG. 2 for diagrammatic simplicity, lead 16B may similarly penetrate the bladder wall to dispose electrode 26B within bladder 14 proximate to the interior surface of the bladder wall at a second location. IMD 18 is also electrically coupled to stimulation lead 20 which, although not shown in the figures, terminates at a nerve site, such as the sacral nerve that innervates the urinary sphincter. Stimulating the sacral nerve may, for example, cause the sphincter to contact and help patient 12 avoid urinary incontinence events. While both leads 20 and 16 carry electrical current, the electrical signals are different from each other and are generated for different purposes. The electrical signal carried by leads 16 is emitted into bladder 14 by electrode 26A, and received by electrode 26B on the opposite side of the wall of bladder 14.

Leads 16 are tunneled through the abdominal cavity of patient 12 to reach bladder 14. Leads 16 are placed within respective small holes within bladder wall 28 in order for electrodes 26 to reside within bladder 14. Electrodes 26 and leads 16 plug the holes in bladder wall 28 and effectively seal urine within bladder 14. Electrodes 26 are secured within bladder wall 28 to prevent the movement of leads 16 as bladder wall 28 expands and contracts with filling and voiding cycles of bladder 14. In addition, leads 16 include either extra length of lead or a flexible material to allow leads 16 to move with the changing size of bladder 14. An inflexible or taught lead 16 could damage the lead, IMD 18 or patient 12. As described above, the invention is not limited to embodiments in which electrodes 26 are located inside bladder 16. In some embodiments, leads 16 may attach to the outside of bladder wall 28, disposing electrodes 26 proximate to or embedded within the wall, but outside the bladder cavity.

Leads 16 may include fixation elements, such as barbs, hooks, an expandable, stent-like element, or an expandable hydrogel element to maintain electrodes 26 in desired positions, and prevent the electrodes from withdrawing from bladder 14. An expandable, stent-like or hydrogel element, or a biological glue, may plug the hole formed by insertion of electrodes 26 and leads 16 through bladder wall 28. Such elements or glues may be located inside or outside of bladder 14 when electrodes 26 are positioned within bladder. Leads 16 and electrodes 26 may be advanced into bladder 14 via a hollow, rigid catheter, needle, or the like, which penetrates bladder wall 28, and expansion of a stent-like or hydrogel element may occur after the catheter or needle is withdrawn. Leads 16 may be formed to include a helical section that provides "slack" to allow leads 16 to move with the changing size of bladder 14.

IMD 18 may be located near bladder 14 or sacral nerve. Shorter leads 20 and 16 may reduce the risk of patient infection, tissue disturbance and signal noise. In other embodiments, IMD 18 may wirelessly communicate with a separate implantable stimulation device located near the sacral nerve and an implanted sensor module that detects the impedance through bladder 14. In such embodiments, IMD 18 may be located in any convenient location that facilitates wireless communication, and need not be coupled to leads 16, 20.

Figure 3:
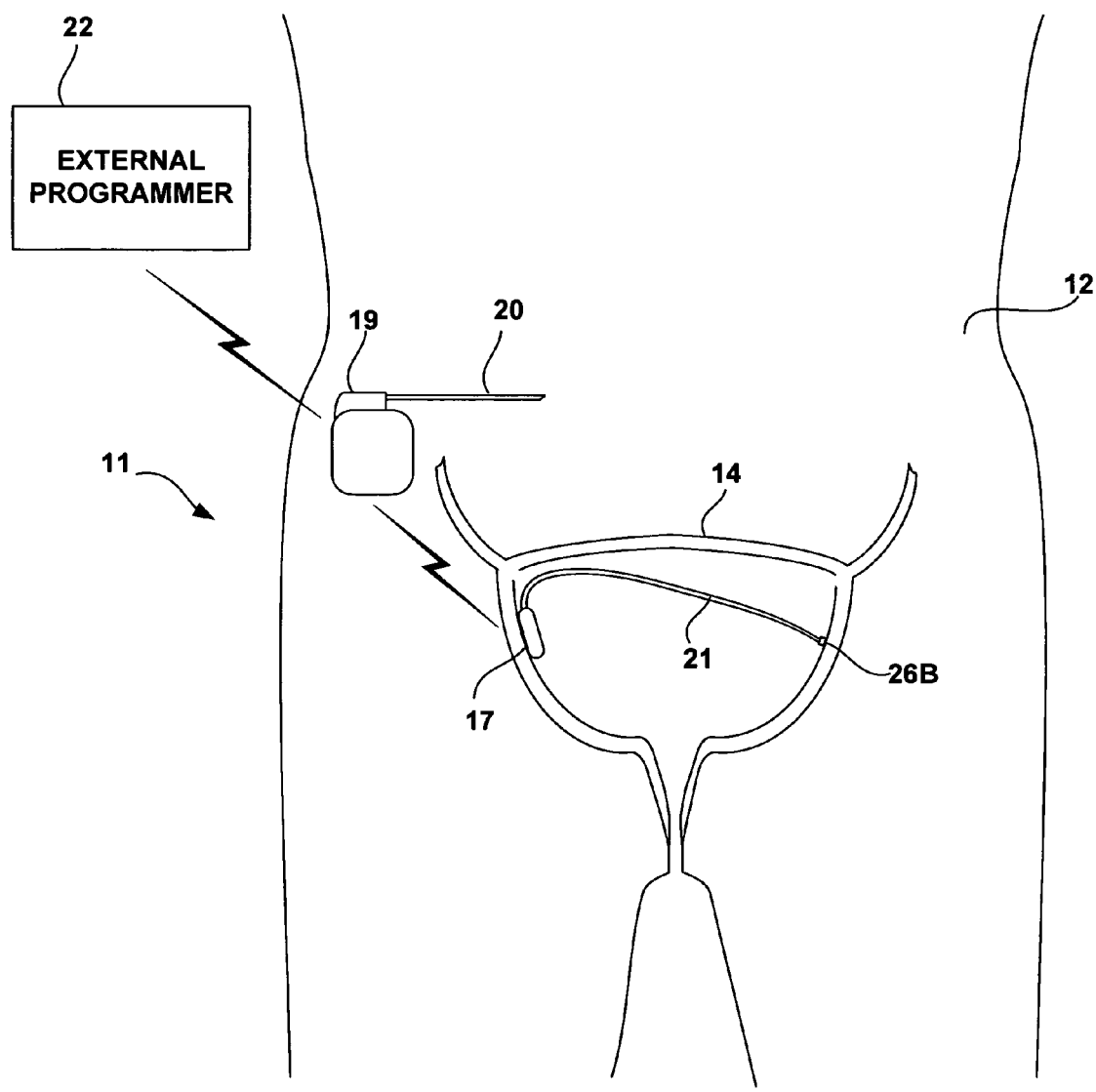
FIG. 3 is a schematic diagram illustrating another example system that senses parameters of the bladder based on an impedance through the bladder.

FIG. 3 is a schematic diagram illustrating an implantable stimulation system 11, incorporating an IMD 19, and a wireless implantable sensor module 17 that detects an impedance through the bladder. As shown in FIG. 3, system 11 also includes an IMD 19 coupled to a lead 20, and an external programmer 22, which are substantially similar to external programmer 22, IMD 18 and lead 20 described above with reference to FIGS. 1 and 2. In the illustrated embodiment, module 17 is implanted inside bladder 14 at a first location, and includes a first electrode 26A (not shown in FIG. 3), e.g., formed on its housing. The first and second electrodes are located at first and second positions proximate to the interior surface of bladder 14 and, as shown in FIG. 3, may be located substantially opposite each other relative to a center of bladder 14. In other embodiments, module 17 and electrodes 26 may be located outside of bladder 14 proximate to the bladder wall, e.g., attached to the exterior surface of the wall. Further, in some embodiments, module 17 may be coupled to both electrodes 26 via respective leads or a common lead, or may both be formed on or within a housing of the module.

Module 17 may transmit an electrical signal through bladder 14 via first and second electrodes 26, and detect an impedance through the bladder based on the signal. Module 17 may be capable of wireless communication with either or both of IMD 19 and external programmer 22 for transmission of information relating to the detected impedance, such as impedance measurements or bladder parameter values derived from such measurements. IMD 19 and/or external programmer 22 may control delivery of therapy by IMD 19 based on the transmitted information, as discussed above with reference to FIG. 1. Further, external programmer 22 may present information relating to bladder filling and emptying to a user, such as a physician, based on the transmitted information, as discussed above with reference to FIG. 1.

IMD 19 may act as an intermediary for communication between module 17 and external programmer 22. Additionally, module 17, IMD 19, and/or external programmer 22 may communicate wirelessly to coordinate transmission of the signal through bladder 14, e.g., to coordinate or request measurements.

As discussed above, some embodiments of the invention need not include a therapy delivering IMD. In other words, in some embodiments, module 17 may support purely diagnostic purposes, such as urodynamic study, e.g., by transmission of information to external programmer 22.

Figure 4:
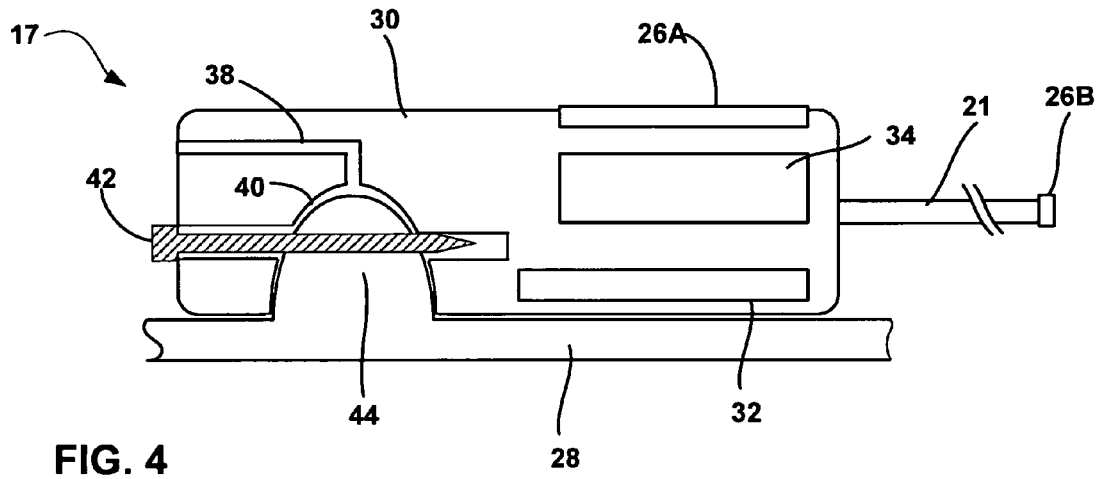
FIG. 4 is a cross-sectional side view of an implantable module attached to the interior wall of the bladder of a patient.

FIG. 4 is a cross-sectional side view of implantable module 17 attached to the interior wall of the bladder of a patient. As shown in FIG. 4, module 17 includes a housing 30 and electrode 26A formed on, as part of, or within the housing. Module 17 is also coupled to electrode 26B by lead 21, as discussed above. Electrodes 26 may be coupled to a circuit board 32 within module 17. A power source 34, such as a battery, may be provided to power circuit board 32 and the components attached thereto. Circuit board 32 may include circuitry to generate the signal transmitted through bladder 14 via electrodes 26, and processing electronics and other circuitry to determine an impedance through the bladder based on the transmitted signal. In addition, circuit board 32 may include telemetry circuitry for wireless telemetry with IMD 19, external programmer 22, or both.

Power source 34 may take the form of a small rechargeable or non-rechargeable battery, which may be configured as a coin cell or pin cell. Different types of batteries or different battery sizes may be used, depending on the requirements of a given application. To promote longevity, power source 34 may be rechargeable via induction or ultrasonic energy transmission, and includes an appropriate circuit for recovering transcutaneously received energy. For example, power source 34 may include a secondary coil and a rectifier circuit for inductive energy transfer. Power generation or charging electronics may be carried on circuit board 32. In still other embodiments, power source 34 may not include any storage element, and module 17 may be fully powered via transcutaneous inductive energy transfer. As a further alternative, IMD 18 or programmer 22 may be configured to apply inductive power to module 17 whenever detection is desired. In this case, when inductive power is not applied, module 17 is asleep. Upon application of inductive power, module 17 wakes up, acquires a sense signal, and transmits the signal to programmer 22 or IMD 19. Accordingly, IMD 19 or programmer 22 determines the sampling rate of module 17 by powering up the module at desired intervals.

Module housing 30 may be made from a biocompatible material such as titanium, stainless steel or nitinol, or a polymeric material such as silicone or polyurethane. Another material for fabrication of housing 30 is a two-part epoxy. An example of a suitable epoxy is a two-part medical implant epoxy manufactured by Epoxy Technology, Inc., mixed in a ratio of 10 grams of resin to one gram of activator. In general, housing 30 contains no external openings, with the exception of openings to facilitate connection of conducts that are coupled to electrodes to circuit board 32 within the housing. The openings may be a hermetically sealed feedthroughs, allowing housing 30 to protect power source 34 and circuit board 32 from the environment within bladder 14.

In some embodiments, housing 30 may have a capsule-like shape with a length in a range of approximately 2 to 15 mm, a width in a range of approximately 2 to 10 mm, and a height in a range of approximately 2 to 10 mm. The capsule-like shape may produce a circular cross-section, in which case housing 30 may have a diameter of approximately 3 to 10 mm, rather than width and height dimensions.

Attaching implantable module 17 to the interior bladder wall 28 of bladder 14 may be accomplished in a variety of ways, but preferably is completed in a manner that will not excessively injure bladder 14 or otherwise cause excessive trauma during implantation. Preferably, attachment should cause limited inflammation and substantially no adverse physiological modification, such as tissue infection or a loss in structural integrity of bladder 14. However, it is desirable that implantable module 17 also be attached securely to the attachment site in order to provide an extended period of measurement without prematurely loosening or detaching from the intended location.

As an example, housing 30 may define a vacuum cavity 40 and vacuum channel 38. A vacuum is created in vacuum cavity by a deployment device having a vacuum line in communication with vacuum channel 38. The vacuum draws tissue 44 from bladder wall 28 into vacuum cavity 40. Vacuum cavity 40 may be sized to capture a volume of bladder wall tissue on the order of approximately 1 to 5 mm³.

Once tissue 44 of bladder wall 28 is captured within vacuum cavity 40, a fastening pin 42 is driven into the captured tissue to attach sensor housing 30 within bladder 14. Fastening pin 42 may be made from, for example, stainless steel, titanium, nitinol, or a high density polymer. The shaft of pin 42 may be smooth or rough, and the tip may have a sharp point to allow for easy penetration into tissue. Fastening pin 42 may be driven into housing 30 and tissue 44 of bladder wall 28 under pressure, or upon actuation by a push rod, administered by a deployment device. In another embodiment, implantable module 24 may be attached without the use of a penetrating rod but with a spring-loaded clip to pinch trapped bladder wall 28 within cavity 40. A variety of other attachment mechanisms, such as pins, clips, barbs, sutures, helical screws, surgical adhesives, and the like may be used to attach housing 30 to bladder wall 28 of bladder 14.

In the example of FIGS. 3 and 4, housing 30 of implantable module 17 is attached to the interior bladder wall 28 of bladder 14 near the side of the bladder. However, the attachment site for housing 30 could be at any position on bladder wall 28 that does not interfere with bladder function or other organ function. For example, housing 30 may be placed in the top of the bladder or near the urethra. In some patients, the most desirable position may coincide with the least invasive implantation surgery. Placing housing 30 substantially opposite electrode 26B, as illustrated in FIG. 3, may allow more accurate determination of changes in bladder 14 size. Module 17 may be surgically implanted using open surgery or laparoscopic techniques, or may be endoscopically implanted via the urethra.

Figure 5:
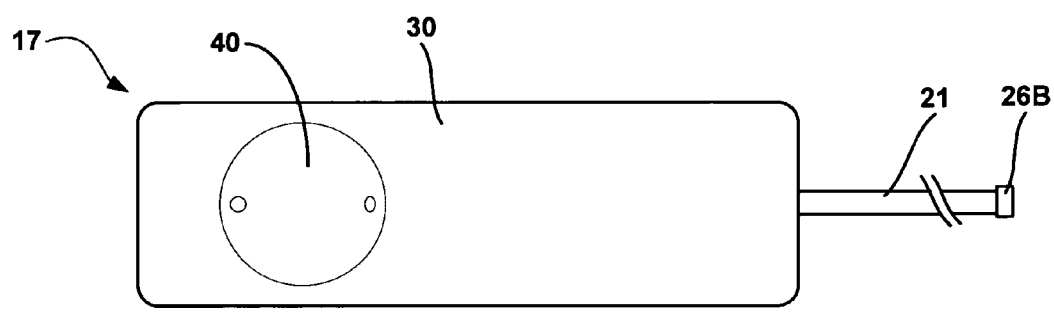
FIG. 5 is a bottom view of the implantable module of FIG. 4.

FIG. 5 is a bottom view of module 17. As discussed above, housing 30 defines vacuum cavity 40, which comes into contact with bladder wall 28 when attaching module 17 to the interior surface of bladder wall 28. Electrode 26A is located on the opposite side of housing 30. However, some embodiments may require electrode 26A to reside on other surfaces of housing 30. In addition, module 17 may include multiple electrodes 26 on more than one surface of housing 30. Additional electrodes may detect different electrical signals simultaneously, provide redundancy if electrode 26A fails to operate correctly, or be used to transmit the signal through bladder without leads 16.

Vacuum cavity 40 holds a portion of tissue from bladder wall 28 in order to keep housing 30 in contact with the interior surface of bladder 14. In some embodiments, housing 30 may contain more than one vacuum cavity to attach to multiple points along bladder wall 28. For example, one vacuum cavity on each end of housing 30 may provide secure contact between the housing and bladder wall 28. In other embodiments, housing 30 may be formed into a different shape than the illustrated rectangular shape. For example, housing 30 may comprise a circular shape or concave shape to better fit the curvature of bladder 14.

Figure 6:
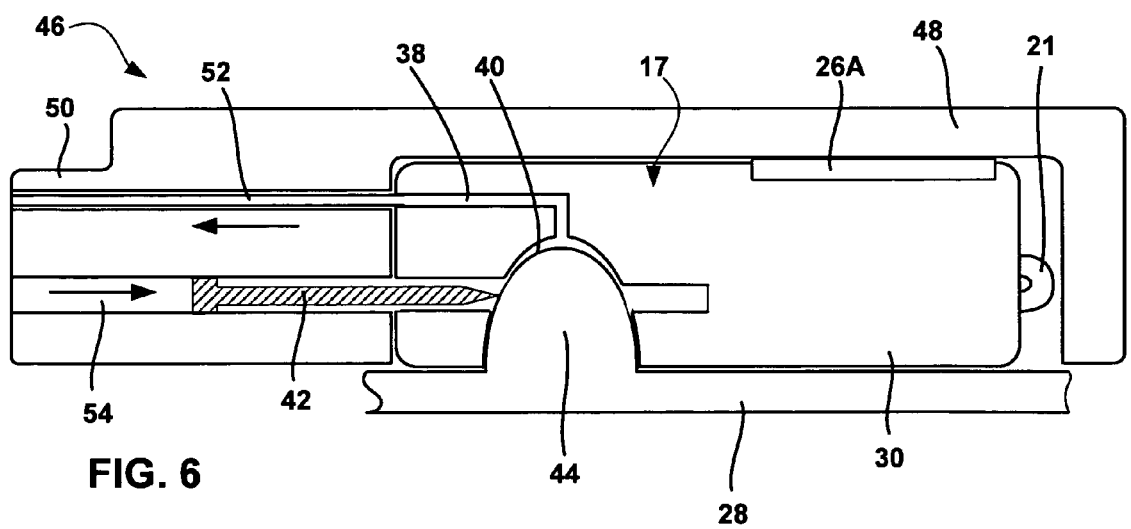
FIG. 6 is a cross-sectional side view of a deployment device during deployment and fixation of the implantable module of FIG. 4.

FIG. 6 is a cross-sectional side view of deployment device 46 used during deployment and fixation of implantable module 17. In the example of FIG. 6, deployment device 46 includes a distal head 48. Distal head 48 may be mounted on an elongated sheath 50 (partially shown in FIG. 6) configured for laproscopic introduction via a trocar, or endoscopic introduction into patient 12 through the urethra. Deployment device 46 may be used with other components, such as a gas distension tube for inflating the pelvic cavity to facilitate access to bladder 14, and a visualization scope for viewing the implantation site. In some embodiments, visualization components may be integrated with deployment device 46. Deployment device may include mechanisms for steering distal head 48 using a proximal handle, as is known in the art.

As shown in FIG. 6, distal head 48 receives a vacuum line 52 and a positive pressure line 54 via elongated sheath 50. Vacuum line 52 is coupled to a vacuum outside of patient 12 via a tube or lumen extending along the length of deployment device 46. Similarly, positive pressure line 54 is coupled to a positive pressure source (not shown) via a tube or lumen extending along the length of deployment device 46. Vacuum line 52 is in fluid communication with vacuum channel 38 and vacuum cavity 40, and permits the physician to draw a vacuum and thereby capture tissue 44 of bladder wall 28 within the vacuum cavity. Positive pressure line 54 permits the physician to apply a pulse of high pressure fluid, such as a liquid or a gas, to drive fixation pin 42 into module housing 30 and through tissue 44 of bladder wall 28. Pin 42 thereby fixes sensor housing 30 to external bladder wall 28. In some embodiments, a membrane mounted over an opening of positive pressure line 54 may be punctured by pin 42.

Once fixation pin 42 attaches module 24 to the interior surface of bladder 14, vacuum line 52 is no longer needed. However, in some embodiments, vacuum line 52 may be used to detach module 24 from distal head 48 of deployment device 46. By terminating vacuum pressure, or briefly applying positive pressure through vacuum line 52, for example, head 42 may separate from module 24 due to the force of the air pressure. In this manner, vacuum line 52 may aid in detachment of module 24 prior to removal of deployment device 46.

As described previously in FIG. 4, fixation pin 42 punctures bladder wall 28 for fixation of module 24. While the force of this fixation may vary with patient 12, deployment device 46 provides adequate force for delivery of pin 42. In an exemplary embodiment, positive pressure line 54 is completely sealed and filled with a biocompatible fluid (such as water, saline solution or air). Sealing the end of positive pressure line 44 is fixation pin 42 or a head on fixation pin 42.

Fixation pin 42 is generally able to move within positive pressure line 54 much like a piston. Force to push fixation pin 42 through tissue 44 of bladder wall 28 captured in vacuum cavity 40 is created by application of a pulse of increased fluid pressure within positive pressure line 54. For example, the physician may control a positive pressure source via control handle attached to deployment device 46. This simple delivery method may provide high levels of force, allow multiple curves and bends in deployment device 46, and enable a positive pressure line 54 of many shapes and sizes.

In an alternative embodiment, a flexible, but generally incompressible, wire may be placed within positive pressure line 54 and used as a push rod to force fixation pin 42 through the captured tissue 44 of bladder wall 28. This wire presents compressive force from the control handle of deployment device 46 directly to fixation pin 42. This method may eliminate any safety risk of pressurized fluids entering patient 12 or, in some embodiments, permit retraction of pin 42 after an unsuccessful fixation attempt. If attached, the flexible wire may be attached to pin 42 and pulled back to remove the pin from tissue 44. The flexible wire may be sheared from fixation pin 42 for detachment purposes as distal head 48 releases sensor 24. This detachment may be facilitated by a shearing element or low shear stress of the wire.

In FIG. 6, deployment device 46 illustrates the attachment of vacuum line 52 and positive pressure line 54 to one end of module 24. In some embodiments, deployment device 46 may attach vacuum line 52 and positive pressure line 54 to their respective channels opening on the top of housing 30 instead of the side of the housing. This change in location may facilitate attachment of module 17 from a variety of locations or on certain locations on the inside surface of bladder 14.

Deployment device 46 may introduced to patient 12 by a small incision in the abdomen of the patient. A surgeon may guide distal head 48 through the abdominal space to a small incision in the bladder 14. Once at bladder 14, the surgeon locates the desired spot for attaching module 24 on the interior surface of the bladder. Module 17 is then pressed up against bladder wall 28 and the vacuum is initiated to bring tissue 44 into vacuum cavity 40 before fixation pin 42 is driven through tissue 44. Deployment device releases module 17 and is removed from patient 12.

In other embodiments, module 17 may be attached to the interior surface of bladder 14 through open abdominal surgery to precisely locate the attachment point within bladder 14. In this type of procedure, deployment device 46 may or may not be used to attach module 24 to bladder wall 28. In still other embodiments, deployment device 46 may be sized and configured for endoscopic insertion into bladder 14 via the urethra. In such embodiments, distal head 48 and module 24 may be advanced and steered to a desired implant location on the interior surface of bladder 14. In some embodiments, endoscopic implantation via the urethra may avoid the need for surgical incisions in the patient and, in particular, the bladder. In some embodiments, deployment device 46 may include a small endoscopic camera in the distal head 48. The camera may enable the physician to better guide deployment device 46 through a small opening in patient 12 to a desired attachment location on the external surface of bladder 14 in less time with more accuracy, as is common in endoscopic surgery. Images may be displayed using video fed to a display monitor.

In the illustrated embodiment, lead 21 is attached to module 17 during implantation of the module. Lead 21 may be located partially or completely within the cavity formed by distal head 48, along with module 17, during implantation. Lead 21 may be initially coiled or otherwise "packaged" within the cavity, or allowed to freely extend outside of the cavity during implantation of module 17.

Although shown as attached to a distal side of module 17, lead 21 may in other embodiments be attached the proximal side of the module, i.e., proximate to cavity 40 formed by the housing of the module. In such embodiments, sheath 50 of delivery device 46 may define a lumen to hold lead during implantation of module 17. As device 46 is withdrawn after implantation of module 17, lead 21 may withdraw from the lumen. In either case, tools may be advanced through a lumen of device 46 or other trocar or endoscopic device for manipulation of lead 21 and electrode 26B to a desired position, e.g., second position, proximate to the bladder wall, and attachment of electrode to the bladder wall at the desired position. In some embodiments, such tools may be used to introduce lead into patient 12 and attach lead to module 17 after implantation of the module. Lead 17 may include hooks, barbs, helical, or screw-like elements for fixation of electrode 26B at a desired position. In some embodiments, electrode 26B may be formed to include such fixation elements.

Distal head 48 may be disposable. Disposable devices that come into contact with patient 12 tissues and fluids greatly decrease the possibility of infection in implantable devices. In other embodiments, the entire deployment device 46 may be manufactured from robust materials intended for multiple uses. The device would then need to be sterilizable between uses. In still a further embodiment, the features of distal head 48 may be incorporated into module 24. In this configuration, module 24 may be larger in size but would include the necessary elements for attachment within the device. After attachment, the entire module would detach from the handle of deployment device 46, reducing the difficulty of removing the entire deployment device 46, including distal head 48.

After the useful life of implantable module 17 is complete, or it is no longer needed within patient 12, the module can be removed from patient 12 in some manner. Alternatively, module 17 may simply remain in place. As an example, deployment device 46 may be reinserted into patient 12, navigated to bladder 14, and reattached to module 17. Deployment device 46 may then be withdrawn from bladder 14, explanting module 17 from patient 12. Alternatively, a surgeon may perform open abdominal surgery to remove the implanted bladder module 24 and IMD 18.

Figure 7:
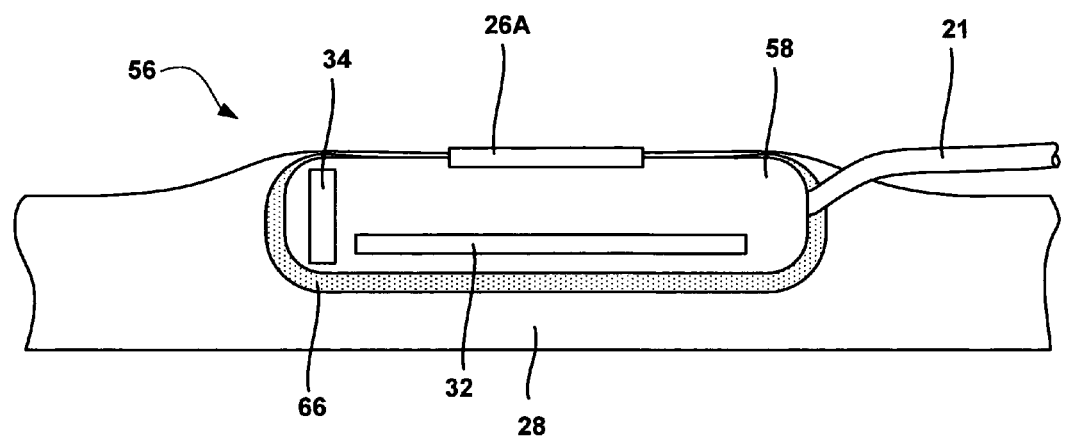
FIG. 7 is a cross-sectional side view of an implantable module placed within the bladder wall of a patient.

FIG. 7 is a cross-sectional side view of another implantable module 56, which is implanted within bladder wall 28 of patient 12. Module 56 includes a housing 58 is in the shape of a rounded capsule and includes a smooth surface. Notably, due to the different in implantation technique of module 56, housing 58 need not include a cavity 40 or vacuum channel 38. Other than these differences, housing 58 may be formed and function substantially similarly to housing 30 of module 17.

Like module 17 of FIGS. 3-6, module 56 includes circuit board 32, power source 34, and electrode 26A, and is coupled to electrode 26B via lead 21. In the illustrated example, housing 58 is partially embedded in bladder wall 28. Module 56 rests in wall cavity 80 formed within bladder wall 28. Module 56 may have a capsule-like shape, and may have a length of approximately 2 to 10 mm, a width of approximately 2 to 5 mm, and a thickness of approximately 1 to 5 mm. The capsule-like shape may produce a circular cross-section, in which case sensor 56 may have a diameter of approximately 1 to 5 mm, rather than width and height dimensions. In some embodiments, module 56 resides completely within wall cavity 80 and does not protrude out of the interior surface of bladder wall 28. Lead 21 may protrude though the bladder wall, or be attached to module at a location that protrudes though the bladder wall.

Figure 8:
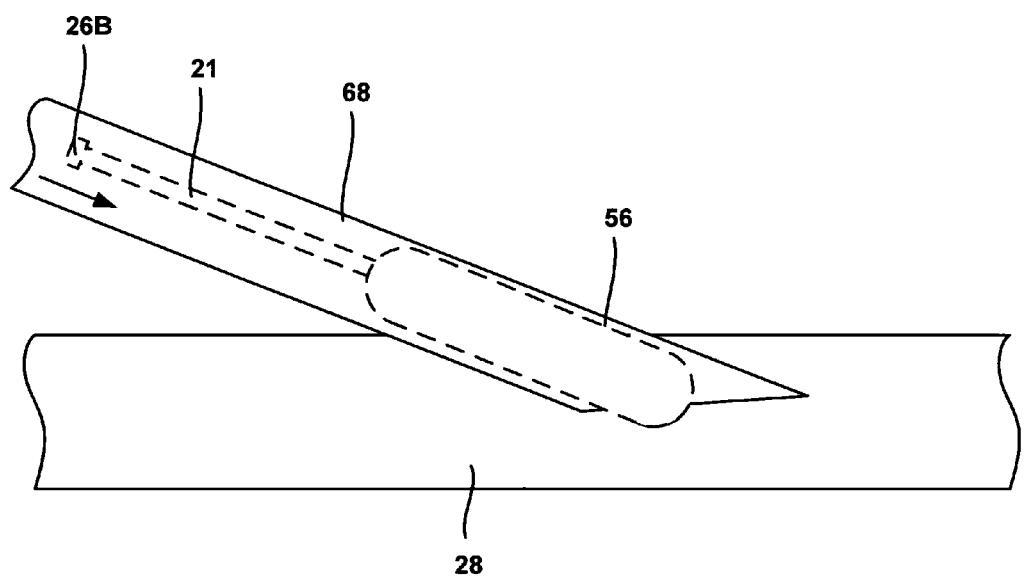
FIG. 8 is a schematic diagram illustrating deployment of the implantable module of FIG. 7.

FIG. 8 is a schematic diagram illustrating endoscopic deployment of implantable module 56. Implantable module 56 may be implanted through endoscopic, laparoscopic, or similar minimally invasive techniques. In some embodiments, a surgeon may make a few small incisions in the abdomen of patient 12 and guides implantable module 56 within a needle 68 to bladder 14 with the aid of a small camera. In other embodiments, needle may be advanced through a lumen of an endoscope or other catheter, through the urethra and into bladder. Needle 68 may be constructed of a metal alloy and comprise a hollow cylinder and a pointed distal end for puncturing bladder wall 28. Needle 68 includes implantable sensor 56 and a fluid to force the sensor out of the needle. An exemplary fluid may be saline or other biocompatible fluid. In some embodiments, needle may also deliver the fluid prior to module 56 to expand cavity 80 within the bladder wall so that it may receive module 56. In other embodiments, needle 68 may comprise a catheter or other hollow delivery vehicle.

Once needle 68 in positioned at the appropriate location of bladder 14, the surgeon may force sensor 56 into place. Removing needle 68 from bladder wall 28 allows the external tissue of bladder wall 28 to close and surround, or partially surround, sensor 56. In some embodiments, the surgeon may suture the insertion hole of bladder wall 28 to promote tissue healing. The suture may comprise resorbable or non-resorbable suture or staples. Care should be taken to avoid unnecessary openings within bladder wall 28 to prevent patient 12 from developing infection or other health problems.

In other embodiments, implantable module 56 may be implanted through more invasive procedures, such as open abdominal surgery which exposes bladder 14. In some embodiments, multiple modules 56 may be placed around bladder 14 to generate distance information around the entire bladder.

In some embodiments, implantable module 56 may carry one or more expandable elements that help to anchor the sensor within the bladder wall. The expandable elements may be constructed from a hydrogel material. During implantation, the expandable elements are in a dehydrated state, in which the expandable elements are smaller. But when implanted in the body of a patient, the expandable elements absorb water from the body tissues and assume a hydrated state. In the hydrated state, the expandable elements have a larger perimeter. Expansion of the expandable elements resists migration of the module 56 within bladder wall 28. After implantation of module 56 separate tools may be advanced through the needle or another instrument to manipulate and place lead at a desired location, as described above with reference to FIG. 6.

Figure 9:
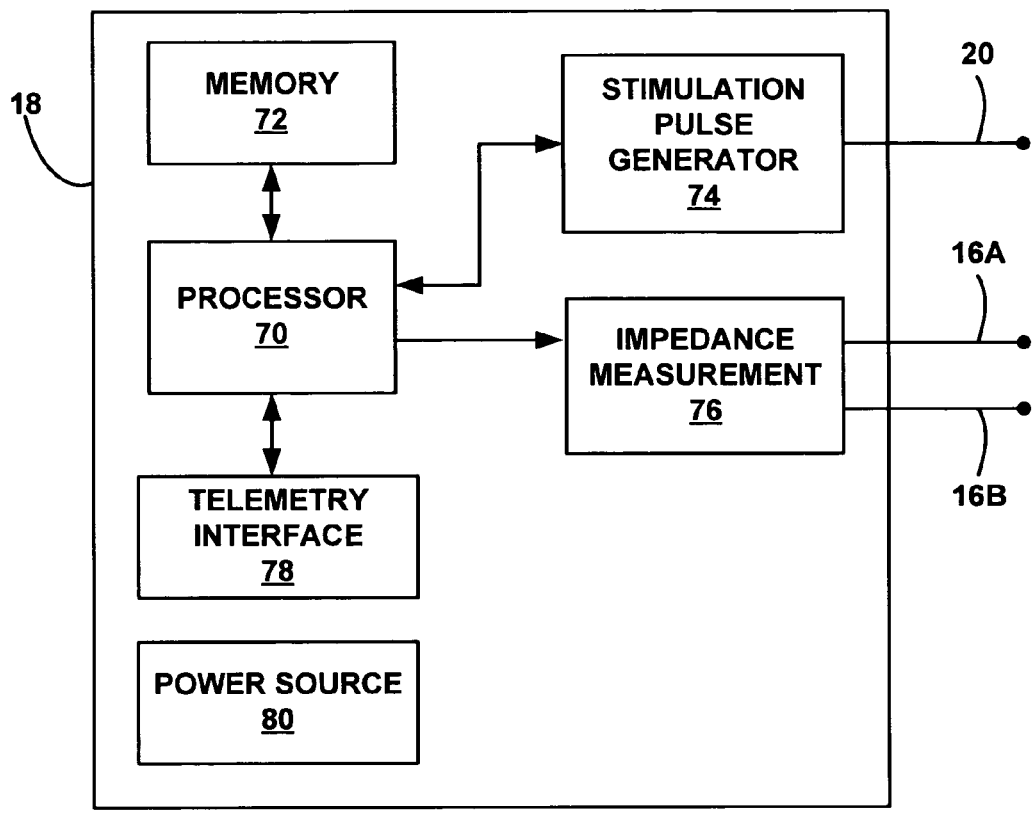
FIG. 9 is a functional block diagram illustrating various components of an implantable medical device which delivers therapy based on a detected impedance through the bladder.

FIG. 9 is a functional block diagram illustrating various components of IMD 18, which is coupled to an electrodes 26 to transmit an electrical signal through bladder, as described above. IMD 19 of FIG. 3 may be configured substantially similar to the example configuration of FIG. 9, except that IMD 19 is not coupled to a leads 16, and therefore would not necessarily include impedance measurement circuitry.

In the example of FIG. 9, IMD 18 includes a processor 70, memory 72, stimulation pulse generator 74, impedance measurement circuitry 76, telemetry interface 78, and power source 80. Memory 72 may store instructions for execution by processor 70, stimulation therapy data, such as stimulation parameter sets and thresholds, functions or look-up tables used to control therapy delivery based on detected impedance, information describing the electrical signal to be transmitted via electrodes 26, and stored information related to detected impedance. Information related to detected impedances may be recorded for long-term storage and retrieval by a user, or used by processor 70 for adjustment of stimulation parameters, such as amplitude, pulse width or pulse rate. Memory 72 may include separate memories for storing instructions, electrical signal information, stimulation therapy data, and bladder information.

Processor 70 controls stimulation pulse generator 74 to deliver electrical stimulation therapy via one or more leads 20. Stimulation pulse generator 74 may include voltage or current sources known in the art for generating stimulation. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 100 microseconds and 1000 microseconds, and still more preferably between approximately 180 microseconds and 450 microseconds.

Processor 70 also controls impedance measurement circuitry 76 to transmit an electrical signal through bladder via leads 16 and electrodes 26. Processor 70 requests impedance measurement circuitry 76 to transmit an electrical signal whenever a bladder measurement is desired. Impedance measurement circuitry 76 may include a voltage or current source, and may include an oscillator or the like for producing an alternating signal, as is known in the art. Impedance measurement circuitry 76 may also include resistors capacitors and other known circuits and components for measuring the current and/or voltage of the signal, as well as processing circuitry for determining the impedance based on measured currents and/or voltages. Processor 70 may include any one or more of a microprocessor, ASIC, DSP, or other digital logic circuitry. In some embodiments, the processing circuitry of impedance measurement circuitry 76 that determines an impedance based on a measured voltage and/or current of a signal may be the same microprocessor, ASIC, DSP, or other digital logic circuitry that forms at least part of processor 70.

Processor 70 may interpret the detected impedance, and determine whether any therapy parameter adjustments should be made. For example, processor 70 may compare the impedance or a bladder parameter value derived therefrom to one or more thresholds, and then take action to adjust stimulation parameters based on the comparison. Processor 70 modifies parameter values stored in memory 72 in response to the detected impedance, either independently or in response to programming changes from external programmer 22. Stimulation pulse generator 74 provides electrical stimulation according to the stored parameter values via one or more leads 20 implanted proximate to a pelvic nerve, such as a sacral or pudendal nerve, or muscle. Processor 70 determines any parameter adjustments based on the detected impedance, or bladder parameter values derived therefrom, and loads the adjustments into memory 72 for use in delivery of stimulation.

The thresholds stored in memory 72 and used to control delivery of therapy based on impedance may be determined based on calibration. In some embodiments, the thresholds may be determined during implantation of IMD 18. For example, during implantation a surgeon may empty bladder to identify a lower limit threshold impedance value associated with low bladder volume, and fill the bladder to identify an upper limit impedance value associated with high bladder volume. Such lower and upper limits may be associated with low intensity and high intensity stimulation levels, used to interpolate intermediate thresholds and stimulation levels. Further, such thresholds may be identified or adapted over time based on user input, e.g., via programming device 22, which may indicate whether the bladder has been emptied or feels full, or an incontinence event has occurred. Processor 70, or a processor of another computing device, such as external programmer 22, may determine the thresholds during calibration.

As an example, if the impedance indicates a contraction of bladder 14 without the approval of patient 12, processor 70 may increase the amplitude, pulse width or pulse rate, or change electrode combination or polarity, of the electrical stimulation applied by stimulation pulse generator 74 to increase stimulation intensity, and thereby increase sphincter closing pressure or pelvic floor tone. If the impedance indicates that bladder size stays constant, processor 70 may implement a cycle of downward adjustments in stimulation intensity until bladder contraction is evident, and then incrementally increase the stimulation upward until expansion begins. In this way, processor 70 converges toward an optimum level of stimulation for purposes of patient comfort and power efficiency. Although processor 70 is described as adjusting stimulation parameters, adjustments alternatively may be generated by a processor of programmer 22 and transmitted to processor 70 via telemetry interface 78 as parameter or program changes.

Bladder size may change due to a variety of factors, such as an activity type, activity level or posture of the patient 12. Hence, for a given set of stimulation parameters, the efficacy of stimulation may vary in terms of rate of bladder expansion or contraction, due to changes in the physiological condition of the patient. For this reason, the continuous or periodic availability of bladder impedance measurements is highly desirable.

By monitoring the impedance though bladder, IMD 18 is able to respond to changes in bladder size with dynamic adjustments in the stimulation parameters delivered to patient 12. In particular, processor 70 is able to adjust parameters in order to improve pelvic floor tone or cause constriction of the urinary sphincter and thereby avoid involuntary leakage. In some cases, the adjustment may be nearly instantaneous to prevent leakage. As an example, if patient 12 laughs, coughs, or bends over, the resulting force on bladder 14 could overcome the closing pressure of the urinary sphincter. If the detected impedance indicates an abrupt change in bladder contraction, however, stimulator 14 can quickly respond by more vigorously stimulating the sacral nerves to increase sphincter closing pressure.

In general, if bladder 14 is contracting for an unknown reason, processor 70 may dynamically increase the level of therapy to be delivered to prevent or stop the voiding of bladder 14. Conversely, if bladder 14 is expanding consistently, processor 70 may incrementally reduce stimulation, e.g., to conserve power resources, until the bladder reaches a fill stage that correlates with the need to void and, thus, a possible incontinence event. Increases or reductions in the level of therapy may include upward or downward adjustments in amplitude (current or voltage), pulse width, or pulse rate of stimulation pulses delivered to the patient.

Telemetry interface 78 may include circuitry to support telemetry communication by radio frequency (RF) communication or proximal induction, as is known in the art. Power source 80 of IMD 18 may be constructed somewhat similarly to power source 34. For example, power source 80 may be a rechargeable or non-rechargeable battery, or alternatively take the form of a transcutaneous inductive power interface.

Figure 10:
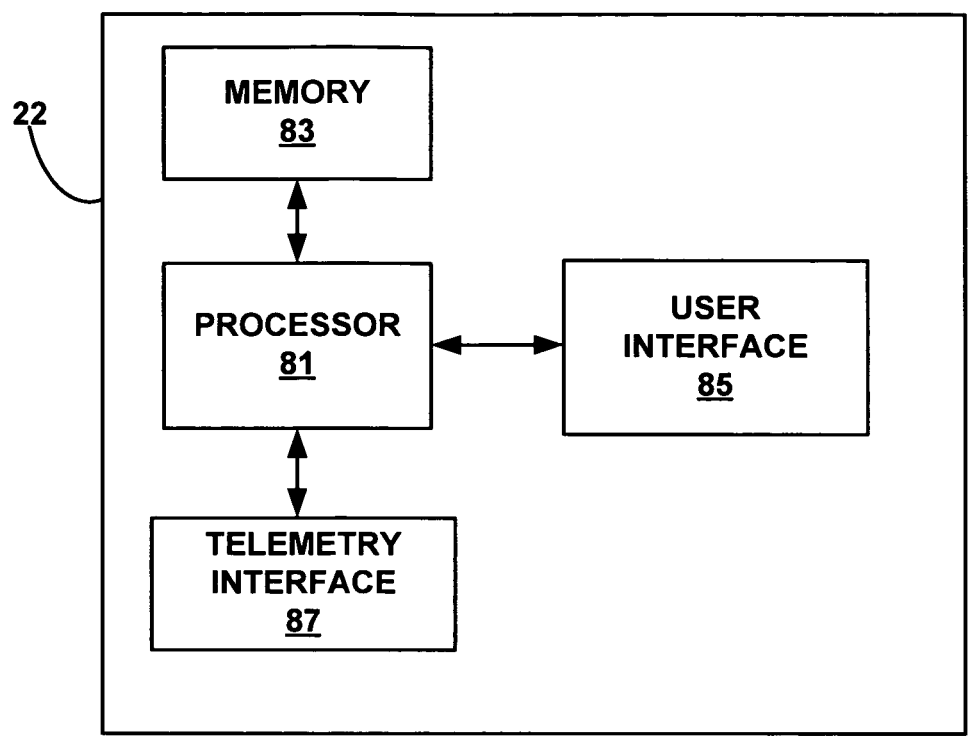
FIG. 10 is a functional block diagram illustrating various components of an example external programmer.

FIG. 10 is a functional block diagram illustrating various components of an example external programmer 22. As illustrated in FIG. 10, external programmer 22 may include a processor 81, memory 83, user interface 85 and telemetry interface 85. Memory 83 may store program instructions that, when executed by processor 81, cause processor 81 and external programmer 22 to provide the functionality ascribed to the external programmer herein.

User interface 85 may include a button or keypad, lights, a speaker, and display, such as a liquid crystal (LCD), light-emitting diode (LED), or cathode ray tube (CRT) display. As discussed herein, processor 81 may present information relating to detected impedance, bladder parameters such as volume, or bladder filling and emptying via the user interface 85. Processor 81 may provide alerts related to bladder volume to patient 12, as described herein, via user interface 85. Although not shown, external programmer 22 may additionally or alternatively include a data or network interface to another computing device, to facilitate communication with the other device, and presentation of information relating to detected impedance, bladder parameters such as volume, or bladder filling and emptying via the other device.

Further, processor 81 may receive information related to detected impedance from IMD 18 or module 17 via telemetry interface 87, adjust therapy based on the detected impedance through communication with IMD 18 or 19 via the telemetry interface. Telemetry interface 87 may be substantially similar to telemetry interface 78 described above, providing wireless communication via an RF or proximal inductive medium. Patient 12 may indicate an intent to void, and processor 81 may effect a blanking interval for the detected impedance, either within external programmer 22, or through communication of the indication to IMD 18, 19 or module 17 via the telemetry interface. Processor 81 may also request impedance detection through communication with IMD 18 or module 17 via the telemetry interface.

Figure 11:
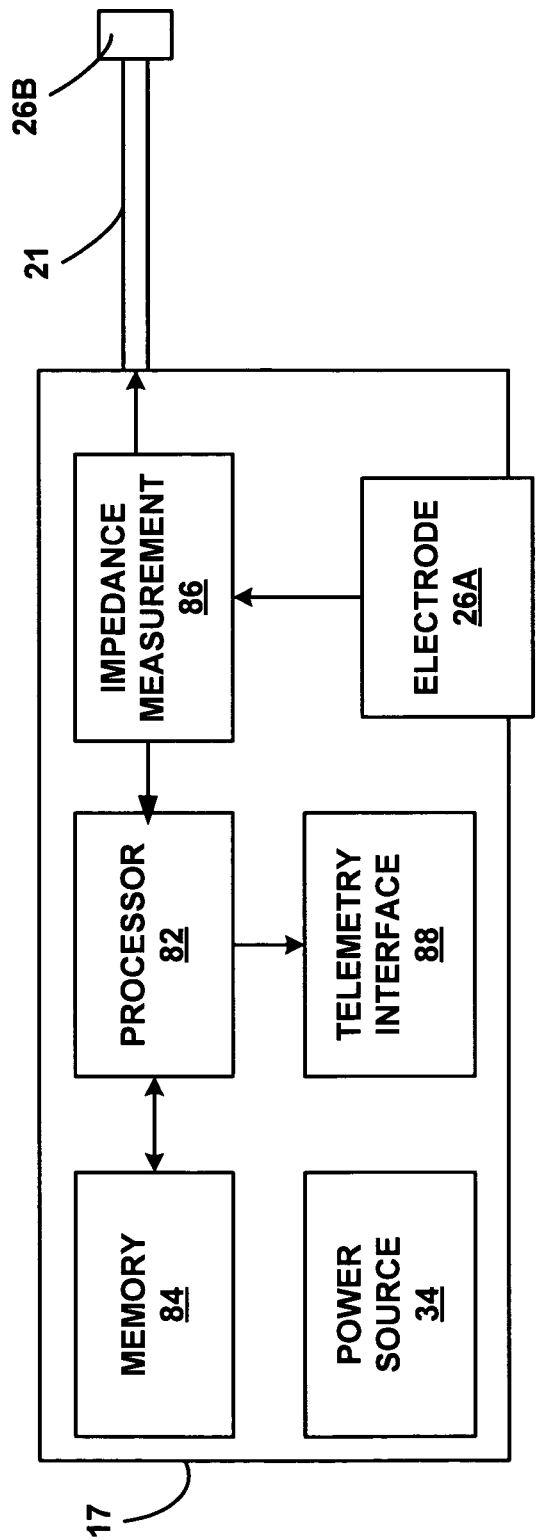
FIG. 11 is a functional block diagram illustrating various components of an example implantable module that includes an electrode.

FIG. 11 is a functional block diagram illustrating various components of an example implantable module 17. Implantable module 56 may be configured substantially similarly to the example configuration of FIG. 11.

In the example of FIG. 11, implantable module 17 includes a processor 82, memory 84, impedance measurement circuitry 86, telemetry interface 88, power source 34 and electrode 26A, and is coupled to electrode 26B by lead 21. Impedance measurement circuitry 86 may be carried on a circuit board, along with processor 82, memory 84 and telemetry interface 88. Impedance measurement circuitry 86 transmits a signal through bladder via electrodes 26, and detects an impedance through the bladder based on the signal that is representative of bladder size, volume, pH, or the like. Impedance measurement circuitry 86 may be substantially similar to impedance measurement circuitry 76 described above with reference to FIG. 9, and may include processing circuitry that also forms at least part of processor 82.

Memory 84 stores instructions for execution by processor 82 and impedance information generated by circuitry 86. Impedance information may then be sent to IMD 19 or external programmer 22 for long-term storage or retrieval by a user. Memory 84 may include separate memories for storing instructions and bladder impedance information. In addition, processor 82 and memory 84 may implement loop recorder functionality in which processor 82 overwrites the oldest contents within the memory with new data as storage limits are met, thereby conserving data storage resources within module 17.

Processor 82 controls telemetry interface 88 to send bladder impedance information to IMD 19 or programmer 22 on a continuous basis, at periodic intervals, or upon request from the IMD or programmer. Wireless telemetry may be accomplished by radio frequency (RF) communication or proximal inductive interaction of module 17 with programmer 22 or IMD 19. Impedance information stored and/or transmitted by module 17 may include impedance measurement samples, or bladder parameter values derived from the detected impedance, such as bladder volume values, rate of bladder volume change values, or pH values. In order to determine bladder parameters, such as volume, based on detected impedance, memory 84 may store thresholds or other calibration information determined during implantation or adaptively during use of module 17, as described above with reference to IMD 18 and FIG. 9.

Power source 34 delivers operating power to the components of implantable module 17. As mentioned previously, power source 34 may include a small rechargeable or non-rechargeable battery and a power generation circuit to produce the operating power. Recharging may be accomplished through proximal inductive interaction between an external charger and an inductive charging coil within module 17. In some embodiments, power requirements may be small enough to allow module 17 to utilize patient motion and implement a kinetic energy-scavenging device to trickle charge a rechargeable battery. In other embodiments, traditional batteries may be used for a limited period of time. As a further alternative, an external inductive power supply could transcutaneously power module 17 whenever impedance measurements are needed or desired.

Figure 12:
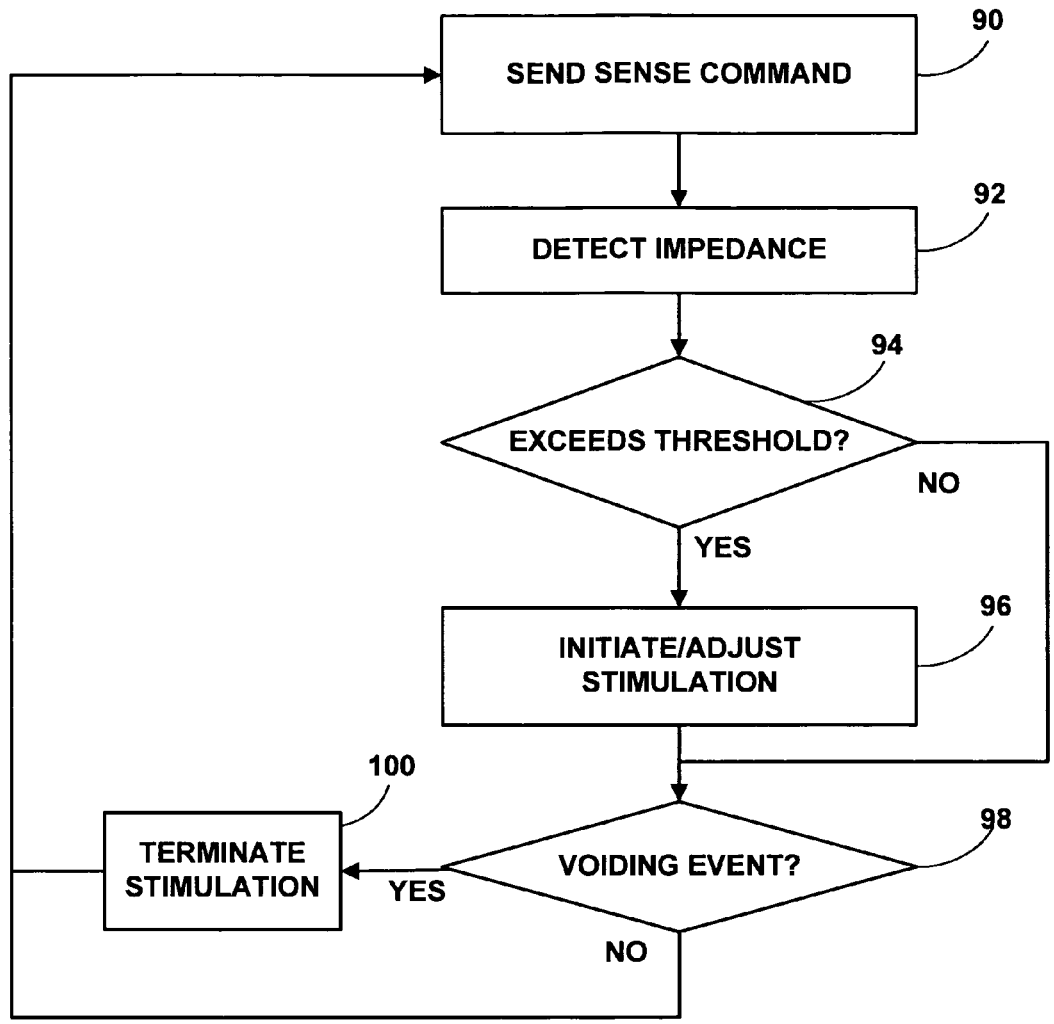
FIG. 12 is a flow chart illustrating an example technique for delivery of therapy based on a detected impedance through the bladder.

FIG. 12 is a flow chart illustrating an example technique for delivery of therapy based on a detected impedance through the bladder. The detected impedance varies based on the volume of the bladder, e.g., the distance across the bladder, and the contents of the bladder, e.g., the urine. As bladder 14 fills with urine, this distance between first and second electrodes 26 increase and can be used to determine the fill state of the bladder. For example, gradual expansion may indicate a gradual filling of bladder 14, while a rapid or instantaneous change may indicate a bladder muscle contraction and the possibility of imminent, involuntary voiding. In other embodiments, the impedance of the electrical signal through bladder 14 may be used to determine the pH of the urine. The pH may be used to determine other bladder activities such as filling or patient diet.

IMDs or modules according to the invention may be able to sense small changes in the impedance through bladder 14. These small changes may be representative of distance resolution of less than one millimeter and as great as tens of centimeters. In some cases, the distance may be directly correlated to the actual bladder volume to track the precise amount and rate of urine being deposited into bladder 14. This information may be utilized in trend information for diagnosing patient conditions, and/or for modulating a urinary incontinence therapy.

An IMD, separate module, or external programmer may use the detected impedance to sense a urine fill stage of bladder 14, which may be indicative of progression toward a voiding event, or a muscle contraction, which may be indicative of an imminent voiding event. The impedance may be monitored for rapid or instantaneous changes indicative of bladder contraction, as well as slow, gradual changes indicative of bladder filling. Rapid and gradual changes may both indicate progression of the bladder toward an imminent voiding event. For example, a decrease in bladder volume may result in an immediate leakage of urine, while bladder filling may result in an eventual leakage of urine when the bladder becomes too full. In both cases, activation or adjustment of electrical stimulation may be desirable to prevent involuntary leakage.

An implantable module, IMD or external programmer may collect, transmit or respond to samples of the detected impedance, or other information determined by based on the impedance. Examples of other information determined based on the detected impedance include bladder volume or activity measurements, rate of bladder volume change, pH, or information indicating a bladder condition, such as a state of fullness, or contraction. As the fill stage increases, an IMD may apply progressively greater levels of stimulation to prevent an involuntary voiding event, i.e., unintended bladder leakage. Accordingly, the IMD, either independently or under control of a programmer, may adjust the stimulation level based on the increased impedance through the bladder, which indicates increased bladder volume. The IMD or the programmer may also take certain actions if the detected signal indicates a particular fill stage, and may adjust the stimulation level in steps over a series of sensed fill stages. The stimulation level may be adjusted in discrete steps, or in proportion to a sensed fill stage.

For gradual deformation, indicative of a fill stage, the IMD or programmer may compare the present impedance or fill level to a threshold level, on an absolute basis. The IMD or programmer may modify stimulation based upon this absolute impedance, volume or fill level or upon the rate of the impedance change or filling. For example, if the rate of filling increases and the volume of bladder 14 is already increased, the IMD or programmer may increase stimulation earlier than would be signaled by the fill level alone. Also, the IMD or programmer may detect a decreasing volume or rate of volume change as involuntary leaking, and respond by increasing the intensity of stimulation.

Alternatively, the IMD or programmer may use fill stage and rate of volume change as a signal of the end of bladder voiding. A patient may indicate that the bladder is going to be voided via a programmer, and the IMD or programmer may temporarily stop a stimulation intended to promote urinary retention and/or initiate a stimulation intended to promote urination. The IMD or programmer may monitor the voiding event based on the detected impedance, and determine when the bladder is empty or the rate of decreasing bladder volume has become insignificant. Once this occurs, the IMD may initiate stimulation that promotes urinary retention again to avoid any involuntary leakage after the voiding event, and may terminate the stimulation intended to promote urination. In other embodiments, stimulation may be delivered substantially continuously through bladder voiding, with modifications due to voiding or the associated bladder volume change.

As a further alternative, when a patient indicates an intent to void, e.g., by entry of a voiding command into a programmer the IMD or programmer may apply a blanking interval to module 17, 56. During the blanking interval, module 17, 56 does not generate bladder activity signals, or the IMD or programmer ignores bladder activity signals. Consequently, stimulation is not inadvertently adjusted during the blanking interval due to intentional bladder activity initiated by the patient for voiding. In either case, the module, IMD and external programmer may serve to prevent involuntary leakage and provide the patient with sufficient time to arrive at a restroom for voluntary voiding, either directly or by catheterization. In some embodiments, the IMD, module or programmer may detect a rapid decrease in bladder volume based on the detected impedance as voiding or a pre-voiding contraction, and automatically blank the detected impedance in response to the detected rapid decrease in order to avoid inadvertent adjustment of therapy.

Increases in bladder volume may be due to the gradual addition of urine in the bladder or a contraction of muscle in the bladder wall. During the increase in size of bladder, an IMD may provide electrical stimulation to enhance pelvic floor tone or urinary sphincter function, for example, to keep urine within the bladder. In some embodiments, if the detected signal indicates a threshold volume, an external programmer may signal the patient that the bladder should be voided. Once the IMD or programmer receives confirmation from patient that the bladder is to be voided, e.g., by depression of a button on the programmer, the IMD or programmer may temporarily cease stimulation, reduce stimulation intensity, or maintain the present level of intensity to allow urine to exit the bladder. The IMD or programmer may also initiate a different stimulation intended to promote bladder emptying based on the confirmation received from the patient.

Alerting a patient that the bladder has reached a threshold level of fullness may be particularly useful in the case of spinal cord injury patients, who cannot perceive a sensation of bladder fullness. In some embodiments, one or more implantable modules and an external programmer may be used without an IMD to communicate the current status of the bladder to the external programmer, which signals the patient as to the status of the bladder. The external programmer may provide an LCD, LED lights, other display, audio feedback or tactile feedback. The feedback may inform the patient as to how full bladder is, or if it is time to urinate to avoid an incontinence event, pelvic pain, or a dangerously high bladder volume that could result in kidney problems. Moreover, the patient may utilize such a system for planning the ingestion of solid or liquid food. For example, if the bladder is becoming full and bladder voiding is not possible shortly, the patient may stop any drinking or eating activities to help avoid an incontinence event.

The IMD or programmer may control stimulation in a way that is responsive to abrupt indications of bladder activity, e.g., associated with involuntary bladder contractions. Alternatively, or additionally, the IMD or programmer adjusts stimulation gradually in response to gradual changes in bladder volume. In each case, the IMD or programmer may adjust electrical stimulation parameters, such as amplitude, pulse width or pulse rate, to prevent involuntary voiding. In addition to parameter adjustments, adjustment may involve on and off cycling of the stimulation in response to sensed impedance indicative of a particular bladder fill stage. For example, stimulation may be turned off until the sensed impedance exceeds a threshold indicative of a particular bladder size, volume, or fill stage of the bladder, at which time stimulation is turned on. At the same time, stimulation parameters may be further adjusted as the sensed bladder size continues to increase. If an abrupt change in size associated with a bladder contraction is sensed based on the detected impedance, IMD 18, 19 may respond quickly to increase stimulation intensity and thereby prevent involuntary voiding.

The example method illustrated by FIG. 12 will be described with reference to the components of system 11 illustrated in FIG. 3. However, the example method may be performed by any system according to the invention, including system 10 of FIG. 1.

According to the example method, IMD 19 may send a sense command to module 17 (90). The command may awaken module 17 or otherwise alert the module to transmit a signal through bladder 14 via electrodes 26, and detect an impedance through the bladder based on the signal (92). The sending of a sense command may be optional. For example, in other embodiments, module 17 may automatically detect the impedance on a periodic basis, and provide related information to IMD 19 or programmer 22 on a periodic or polled basis.

Module 17 subsequently transmits information related to the detected impedance to IMD 19, e.g., by wireless telemetry. Alternatively, the information may be transmitted from module 17 to external programmer 22. Module 17 may detect signal by sampling a voltage and/or current, and may determine an impedance, bladder volume, or other bladder parameters based on the sampled voltage or current. In other embodiments, module 17 may transmit the sampled voltage or current to IMD 19 or programmer 22 for determination of an impedance, volume, or other bladder parameters.

Upon receiving such bladder information, IMD 19 may compare a voltage, current, impedance, volume, or other bladder parameter to a threshold (94). If, for example, bladder volume, rate of volume change exceeds a threshold, indicating an advanced fill level, the IMD may initiate or adjust the delivered stimulation, e.g., increase stimulation intensity (96). In some embodiments, threshold comparisons may be provided for both fill stage and volume change rate. If either fill stage or volume change rate exceeds an applicable threshold, the stimulation level may be adjusted.

In some embodiments, IMD 19 and programmer 22 may both receive bladder information from module 17. For example, IMD 19 may react to instantaneous changes in bladder condition, while programmer 22 may react to changes in bladder condition over a period of time, e.g., trend data. Alternatively, either of the IMD or programmer may be configured to react to instantaneous and trending bladder changes.

In some embodiments, IMD 19 may communicate with external programmer 22 to check if patient 12 has desired to void the contents of bladder 14 (98). If patient 12 has signaled a voiding event, e.g., via external programmer 22, stimulation may be terminated to enable the patient to urinate (100). After voiding, stimulation may resume at a previous intensity, lower intensity, or may remain off until bladder 14 reaches a particular fill stage, e.g., exceeds a first threshold. In other embodiments, however, as described above, stimulation may continue substantially throughout voiding at the same intensity or other parameters, or with adjustments to the intensity or other parameters.

In some embodiments, module 17 may be used exclusively for monitoring bladder activity without providing feedback for stimulation therapy. In this case, the process represented in FIG. 12 may be much simpler and only include collecting data and sending collected data to external programmer 22 (90 and 92). Bladder parameters may be monitored continuously, intermittently or at the request of IMD 19 external programmer 22. These embodiments may be used for disease diagnosis or condition monitoring and may enable patient 12 to avoid frequent clinic visits and uncomfortable procedures. In some embodiments, the bladder information related to the detected signal may form part of an automated voiding diary that records voluntary voiding events, involuntary voiding events, and bladder activity levels prior to, contemporaneous with, of after such an event.

Figure 13:
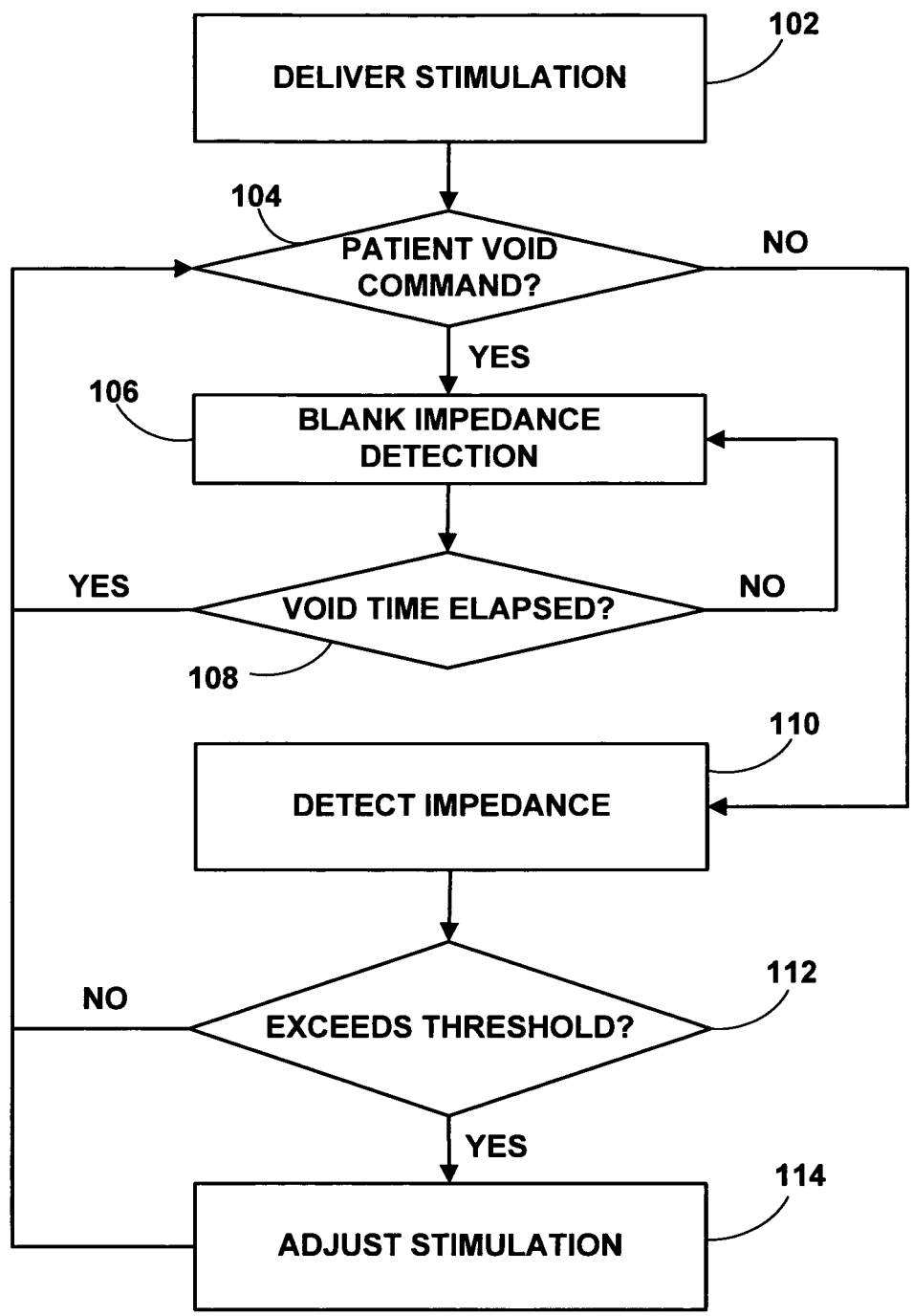
FIG. 13 is a flow chart illustrating another example technique for delivery of therapy based on a detected impedance through the bladder.

FIG. 13 is a flow chart illustrating an alternative technique for delivery of therapy based on a detected electrical signal that indicates an impedance through the bladder. The example technique illustrated by FIG. 13 is described with reference to system 11 of FIG. 3, but may be practiced by any system according to the invention, including system 10 of FIG. 1.

In some cases, stimulation may be delivered at a level that prevents unintentional voiding of urine, but permits the patient to intentionally overcome the stimulation to void urine. Accordingly, stimulation does not necessarily need to be stopped for intentional voiding. However, it is desirable that the stimulation level not be increased in response to a decrease in bladder volume, e.g., bladder contraction, while the patient is attempting to void urine. For this reason, it may be desirable to apply a blanking interval to module 17. The blanking interval is a period during which module 17 does not detect the signal emitted through the bladder, or any values measured by module 17 are ignored by the module, IMD 19, or programmer 22, so that stimulation is not inadvertently adjusted in response to bladder contraction associated with an intentional voiding event.

As shown in FIG. 13, stimulation is delivered by IMD 19 (102). If a patient void command is received (104), e.g., by user input to an external programmer 22, the programmer 22 or IMD 19 applies a blanking interval to the bladder impedance detection (106). Alternatively, as described above, the IMD, module or programmer may automatically detect a rapid decrease in bladder volume based on the detected impedance as voiding or a pre-voiding contraction, and automatically apply blanking interval to the detected impedance in response to the detected rapid decrease. The blanking interval may be a period during which impedance information transmitted by module 17 is ignored by programmer 22, IMD 19, or both, or impedance detection is not requested by the programmer or IMD. Alternatively, during the blanking interval, programmer 22 or IMD 19 may send a wireless command to actively disable module 17 temporarily.

The blanking interval may extend for a predetermined period of time known to be sufficient to complete voiding. Once the voiding time has elapsed (108), programmer 22 or IMD 19 may again determine whether a patient void command has be entered (104). Another patient void command resets the blanking interval.

If no patient void command has been received (104), monitor 17 detects the impedance (110) and provides bladder information based on the impedance to programmer 22 or IMD 19. The bladder information may be provided on a periodic or polled basis, and may include a voltage, current, impedance, volume, rate of volume change, or other signal or bladder parameters. If the bladder information, such as volume level, rate of volume change, or both, exceeds an applicable threshold (112), programmer 22 or IMD 19 adjusts the stimulation level (114), e.g., by adjusting one of more stimulation pulse parameters such as amplitude, pulse width or pulse rate. The stimulation level is adjusted to a level sufficient to avoid involuntary voiding, i.e., an incontinence event. Upon delivery of the stimulation therapy with the adjusted stimulation level, the process continues. In particular, programmer 22 or IMD 19 may continue to monitor for a patient void command or adjust stimulation.

Various embodiments of the described invention may include processors that are realized by microprocessors, Application-Specific Integrated Circuits (ASIC), Field-Programmable Gate Arrays (FPGA), or other equivalent integrated or discrete logic circuitry. A processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory. Each storage option may be chosen depending on the embodiment of the invention.

Many embodiments of the invention have been described. Various modifications may be made without departing from the scope of the claims. For example, although the invention has been generally described in conjunction with implantable neurostimulation devices, a bladder sensor may also be used with other implantable medical devices, such as electrical muscle stimulation devices, functional electrical stimulation (FES) devices, and implantable drug delivery devices, each of which may be configured to treat incontinence or other conditions or disorders. Further, although electrodes an implantable modules have been primarily illustrated herein as located within the bladder, such modules and electrodes may be located outside the bladder, e.g., attached to an outer surface of the bladder wall.

In some embodiments, an IMD 18, 19, module 17 or external programmer 22 may include additional patient physiological sensors, and signals provided by such sensors may be used in addition to the detected impedance to control delivery of therapy for treating incontinence or blanking the detected impedance signal in the manners described herein. For example, an IMD, module or external programmer may include an accelerometer that indicates the gross level of patient activity or whether the patient is involved in particular activities. Based on high activity or particular activities, such as laughing, an IMD or external programmer may increase therapy intensity to avoid incontinence events that may result from such high activities or particular activities. On the other hand, such high activity or particular activities may affect the detected impedance and render it unreliable as an indicator of bladder parameters. In such cases, an IMD, module or programmer may blank the detected impedance in the manners described herein based on the accelerometer signal. These and other embodiments are within the scope of the following claims.

The invention claimed is:

1. A method comprising:
   emitting an electrical signal from a first electrode implanted proximate to a wall of a bladder of a patient at a first location;
   receiving the electrical signal via a second electrode implanted proximate to the wall of the bladder at a second location; and
   detecting an impedance between the first electrode and second electrode through the bladder based on at least one parameter of the signal,
   wherein the first and second electrodes are located within a volume defined by an inner surface of the wall of the bladder.

2. The method of claim 1, wherein the first and second electrodes are located substantially opposite each other relative to a center of the bladder.

3. The method of claim 1, further comprising controlling delivery of a therapy to the patient based on the detected impedance to alleviate urinary incontinence.

4. The method of claim 3, wherein controlling delivery of a therapy comprises controlling delivery of electrical stimulation to at least one of a pelvic floor nerve or a pelvic floor muscle.

5. The method of claim 3, wherein controlling delivery of a therapy comprises:
   determining whether the bladder has reached a threshold level of fullness based on the detected impedance; and
   one of initiating, terminating, or modifying the therapy based on the determination.

6. The method of claim 3, wherein controlling delivery of a therapy comprises:
   determining whether the bladder is contracting based on the detected impedance; and
   one of initiating, terminating, or modifying the therapy based on the determination.

7. The method of claim 3, wherein controlling delivery of a therapy comprises controlling delivery of the therapy from an implantable medical device to the patient.

8. The method of claim 7, wherein the first and second electrodes are electrically coupled to the implantable medical device via respective leads that attach to the wall of the bladder.

9. The method of claim 7, wherein the first and second electrodes are electrically coupled to an implantable module that is separate from the implantable medical device.

10. The method of claim 1, further comprising presenting information relating to at least one of filling or emptying of the bladder to a user based on the detected impedance.

11. The method of claim 10, further comprising determining whether the bladder has reached a threshold level of fullness based on the detected impedance, wherein presenting information to a user comprising alerting the user that the bladder has reached the threshold level of fullness based on the determination.

12. The method of claim 10, further comprising storing information relating to the impedance over a period of time, wherein presenting information relating to at least one of filling or emptying of the bladder comprises presenting information relating to at least one of filling or emptying of the bladder based on the stored information.

13. The method of claim 1, wherein the first and second electrodes are electrically coupled to an implantable module that is implanted on or within the bladder wall.

14. The method of claim 13, further comprising endoscopically implanting the implantable module.

15. The method of claim 1, wherein the at least one parameter of the signal comprises at least one of voltage of the signal or current of the signal.

16. The method of claim 1, wherein the at least one parameter of the signal is detected using the first and second electrode.

17. A system comprising:
a first electrode configured to be implanted proximate to a wall of a bladder of a patient at a first location;
a second electrode configured to be implanted proximate to the wall of the bladder at a second location; and
impedance measurement circuitry electrically coupled to the first and second electrodes that emits an electrical signal via the first electrode, receives the electrical signal via the second electrode, and detects an impedance between the first electrode and second electrode through the bladder based on at least one parameter of the signal,
wherein the first and second electrodes are configured to be implanted within a volume defined by an inner surface of the wall of the bladder.

18. The system of claim 17, wherein the first and second locations are located substantially opposite each other relative to a center of the bladder.

19. The system of claim 17, further comprising an implantable medical device that delivers a therapy to the patient based on the detected impedance to alleviate urinary incontinence.

20. The system of claim 19, wherein the implantable medical device delivers electrical stimulation to at least one of a pelvic floor nerve or a pelvic floor muscle based on the detected impedance.

21. The system of claim 19, further comprising a processor that determines whether the bladder has reached a threshold level of fullness based on the detected impedance, and one of initiates, terminates, or modifies the delivery of therapy by the implantable medical device based on the determination.

22. The system of claim 19, further comprising a processor that determines whether the bladder is contracting based on the detected impedance, and one of initiates, terminates, or modifies the delivery of therapy by the implantable medical device based on the determination.

23. The system of claim 19, wherein the implantable medical device comprises the impedance measurement circuitry, the system further comprising first and second leads configured to be attached to the bladder wall that electrically couple first and second electrodes, respectively, to the implantable medical device.

24. The system of claim 19, further comprising an implantable module that is separate from the implantable medical device and comprises the impedance measurement circuitry, wherein the first and second electrodes are electrically coupled to the implantable module.

25. The system of claim 17, further comprising a user interface that presents information relating to at least one of filling or emptying of the bladder to a user based on the detected impedance.

26. The system of claim 25, further comprising a processor that determines whether the bladder has reached a threshold level of fullness based on the detected impedance, and alerts the user that the bladder has reached the threshold level of fullness via the user interface based on the determination.

27. The system of claim 26, further comprising:
a memory to store information relating to the impedance over a period of time; and
a processor that presents information to a user relating to at least one of filling or emptying of the bladder via the user interface based on the stored information.

28. The system of claim 17, wherein the at least one parameter of the signal comprises at least one of voltage of the signal or current of the signal.

29. The system of claim 17, wherein the at least one parameter of the signal is detected by the impendence measurement circuit via the first and second electrode.

30. A system comprising:
an implantable module configured to be implanted on or within a wall of a bladder of a patient;
a first electrode electrically coupled to the implantable module and configured to be located proximate to the wall of the bladder at a first location; and
a second electrode electrically coupled to the implantable module and configured to be located proximate to the wall of the bladder at a second location, wherein the implantable module emits an electrical signal via the first electrode, detects the electrical signal via the second electrode, and detects an impedance between the first and second electrodes through the bladder based on at least one parameter of the signal,
wherein the first and second electrodes are configured to be implanted within a volume defined by an inner surface of the wall of the bladder.

31. The system of claim 30, wherein the implantable module comprises a housing, and at least one of the first electrode or second electrode is formed on or within the housing.

32. The system of claim 30, wherein a lead electrically couples at least one of the first electrode or the second electrode to the implantable module.

33. The system of claim 30, wherein the implantable module comprises a housing and the housing comprises a fixation structure configured to affix the housing to the interior surface of the bladder.

34. The system of claim 30, wherein the implantable module comprises a housing, and the housing comprises a vacuum cavity configured to capture a portion of the interior surface of the bladder and a fixation element configured to penetrate the captured portion.

35. The system of claim 30, wherein the implantable module comprises a housing sized for endoscopic implantation on the internal surface of the bladder via a urethra of the patient.

36. The system of claim 30, wherein the implantable module comprises wireless telemetry circuitry, and transmits information via the telemetry circuitry based on the detected impedance.

37. The system of claim 36, further comprising an implantable medical device, wherein the implantable medical device receives the information transmitted by implantable module, and delivers a therapy to alleviate urinary incontinence based on the information.

38. The system of claim 36, further comprising:
an external programmer; and
an implantable medical device that delivers a therapy to treat urinary incontinence, wherein the external programmer receives the information transmitted by the implantable module and controls delivery of the therapy by the implantable medical device based on the information.

39. The system of claim 36, further comprising an external programmer that receives the information transmitted by the implantable module, and presents information relating to at least one of filling or emptying of the bladder to at least one of the patient or another user based on the information transmitted by the implantable module.

40. The system of claim 30, wherein the implantable module comprises a memory to store the information relating to the detected impedance.

41. The system of claim 30, wherein the at least one parameter of the signal comprises at least one of voltage of the signal or current of the signal.

42. The system of claim 30, wherein the at least one parameter of the signal is detected by the implantable module via the first and second electrodes.

\* \* \* \* \*